(12) United States Patent
Updyke et al.

(10) Patent No.: US 8,580,112 B2
(45) Date of Patent: Nov. 12, 2013

(54) DIALYSIS SYSTEMS AND METHODS

(75) Inventors: Palmer David Updyke, Walnut Creek, CA (US); Harold Frederick Sandford, Groton, MA (US); Benjamin Joseph Lipps, Boston, MA (US); Douglas Mark Zatezalo, Allison Park, PA (US); Michael James Beiriger, Pittsburgh, PA (US); James Matthew Mullner, Butler, PA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 945 days.

(21) Appl. No.: 12/271,359

(22) Filed: Nov. 14, 2008

(65) Prior Publication Data

US 2009/0127193 A1   May 21, 2009

Related U.S. Application Data

(60) Provisional application No. 61/003,429, filed on Nov. 16, 2007.

(51) Int. Cl.
  *B01D 61/26* (2006.01)
  *B01D 61/28* (2006.01)
  *A61M 37/00* (2006.01)

(52) U.S. Cl.
  USPC ............... 210/321.71; 210/646; 604/5.01; 604/5.04; 604/29; 604/93.01

(58) Field of Classification Search
  None
  See application file for complete search history.

(56) References Cited

U.S. PATENT DOCUMENTS

| | | |
|---|---|---|
| 3,871,913 A | 3/1975 | Shaldon |
| 4,174,231 A | 11/1979 | Hobgood |
| 4,191,351 A | 3/1980 | Goyne |
| 4,581,141 A | 4/1986 | Ash |
| 4,666,598 A | 5/1987 | Heath et al. |
| 4,684,460 A | 8/1987 | Issautier |
| 4,728,496 A | 3/1988 | Petersen et al. |
| 4,770,787 A | 9/1988 | Heath et al. |
| 4,784,495 A | 11/1988 | Jonsson et al. |
| 4,789,467 A | 12/1988 | Lindsay et al. |
| 4,997,577 A | 3/1991 | Stewart |
| 5,256,371 A | 10/1993 | Pippert |
| 5,262,068 A | 11/1993 | Bowers et al. |

(Continued)

FOREIGN PATENT DOCUMENTS

| | | |
|---|---|---|
| EP | 0 278 100 | 8/1988 |
| EP | 0 673 658 | 9/1995 |

(Continued)

OTHER PUBLICATIONS

International Search Report and Written Opinion, PCT/US2008/083554, mailed Jul. 24, 2009.

(Continued)

*Primary Examiner* — Krishnan S Menon
(74) *Attorney, Agent, or Firm* — Fish & Richardson P.C.

(57) ABSTRACT

This disclosure generally relates to dialysis systems and related methods. In one aspect of the invention, a dialysis system includes a device configured so that a medical fluid can pass therethrough, and the device is adapted to remove one or more substances from the medical fluid as the medical fluid passes through the device. The dialysis system can also include a sodium control system adapted to alter a sodium concentration of the medical fluid.

46 Claims, 11 Drawing Sheets

(56) References Cited

U.S. PATENT DOCUMENTS

| | | |
|---|---|---|
| 5,277,820 A | 1/1994 | Ash |
| 5,304,349 A | 4/1994 | Polaschegg |
| 5,409,612 A | 4/1995 | Maltais et al. |
| 5,421,813 A | 6/1995 | Ohnishi |
| 5,536,412 A | 7/1996 | Ash |
| 5,589,070 A | 12/1996 | Maltais et al. |
| 5,591,344 A | 1/1997 | Kenley et al. |
| 5,603,902 A | 2/1997 | Maltais et al. |
| 5,605,630 A | 2/1997 | Shibata |
| 5,713,125 A | 2/1998 | Watanabe et al. |
| 5,788,099 A | 8/1998 | Treu et al. |
| 5,919,369 A | 7/1999 | Ash |
| 5,944,684 A | 8/1999 | Roberts et al. |
| 6,000,567 A | 12/1999 | Carlsson et al. |
| 6,036,858 A | 3/2000 | Carlsson et al. |
| 6,086,753 A | 7/2000 | Ericson et al. |
| 6,143,181 A | 11/2000 | Falkvall et al. |
| 6,170,785 B1 | 1/2001 | Lampropoulos |
| 6,190,855 B1 | 2/2001 | Herman et al. |
| 6,277,277 B1 | 8/2001 | Jacobi et al. |
| 6,280,632 B1 | 8/2001 | Polaschegg |
| 6,308,721 B1 | 10/2001 | Bock et al. |
| 6,409,699 B1 | 6/2002 | Ash |
| 6,416,293 B1 | 7/2002 | Bouchard et al. |
| 6,428,706 B1 | 8/2002 | Rosenqvist et al. |
| 6,484,383 B1 | 11/2002 | Herklotz |
| 6,672,841 B1 | 1/2004 | Herklotz et al. |
| 6,743,201 B1 | 6/2004 | Dönig et al. |
| 6,755,976 B2 | 6/2004 | Rosenqvist et al. |
| 6,878,283 B2 | 4/2005 | Thompson |
| 7,033,498 B2 | 4/2006 | Wong |
| 7,077,956 B2 | 7/2006 | Rovatti |
| 7,241,272 B2 | 7/2007 | Karoor et al. |
| 7,789,849 B2 | 9/2010 | Busby et al. |
| 7,947,179 B2 | 5/2011 | Rosenbaum et al. |
| 8,235,931 B2 | 8/2012 | Burbank et al. |
| 2002/0079695 A1 | 6/2002 | Campbell et al. |
| 2003/0105424 A1 | 6/2003 | Karoor et al. |
| 2004/0019312 A1 | 1/2004 | Childers et al. |
| 2004/0050789 A1 | 3/2004 | Ash |
| 2005/0274658 A1 | 12/2005 | Rosenbaum et al. |
| 2007/0158247 A1 | 7/2007 | Carr et al. |
| 2007/0158249 A1 | 7/2007 | Ash |
| 2007/0158268 A1 | 7/2007 | DeComo |
| 2007/0161113 A1 | 7/2007 | Ash |
| 2007/0161941 A1 | 7/2007 | Ash et al. |
| 2007/0181499 A1 | 8/2007 | Roberts et al. |
| 2008/0149563 A1 | 6/2008 | Ash |
| 2008/0177216 A1 | 7/2008 | Ash |
| 2008/0200869 A1 | 8/2008 | Bedingfield |
| 2009/0107902 A1 | 4/2009 | Childers |
| 2009/0114595 A1* | 5/2009 | Wallenas et al. ............ 210/646 |
| 2011/0303588 A1 | 12/2011 | Kelly et al. |

FOREIGN PATENT DOCUMENTS

| | | |
|---|---|---|
| EP | 0947814 A2 | 10/1999 |
| EP | 1 195 171 | 4/2002 |
| EP | 1 342 480 | 9/2003 |
| EP | 1 096 991 | 6/2004 |
| WO | WO 97/02055 | 1/1997 |
| WO | WO 97/02056 | 1/1997 |
| WO | WO 98/17333 | 4/1998 |
| WO | WO 99/37342 | 7/1999 |
| WO | WO 02/30267 | 4/2002 |
| WO | WO 02/043859 | 12/2005 |
| WO | WO 2005/123230 | 12/2005 |
| WO | WO2006088419 A2 | 8/2006 |
| WO | WO 2007/028056 | 3/2007 |
| WO | WO2006036876 A8 | 4/2007 |
| WO | WO 2007/081383 | 7/2007 |
| WO | WO 2007/081384 | 7/2007 |
| WO | WO 2007/081565 | 7/2007 |
| WO | WO 2007/081576 | 7/2007 |

OTHER PUBLICATIONS

"*RX Guide to Custom Dialysis*," COBE Renal Care Inc., Revision E. Sep. 1993.

"*Sorbent Dialysis Pimer*," COBE Renal Care, Inc., Sep. 4, 1993 Ed.

Blumenkrantz et al., "*Artif Organs*," 3(3):230-236, 1978.

Operator's Manual—Fresenius 2008K Hemodialysis Machine (2000).

Sleep Safe Operating Instructions, Part 677 805 1, Fresenius Medical Care, 1st edition, Aug. 2000, 133 pages.

Sleep Safe Technical Manual, Part 677 805 1, Fresenius Medical Care, 1st edition, Aug. 2000, 174 pages.

\* cited by examiner

DIALYSIS SYSTEMS AND METHODS

CROSS-REFERENCE TO RELATED APPLICATIONS

This application claims the benefit of U.S. Application Ser. No. 61/003,429, filed on Nov. 16, 2007, which is incorporated by reference herein.

TECHNICAL FIELD

This disclosure relates to dialysis systems and methods.

BACKGROUND

Renal dysfunction or failure and, in particular, end-stage renal disease, causes the body to lose the ability to remove water and minerals and excrete harmful metabolites, maintain acid-base balance and control electrolyte and mineral concentrations within physiological ranges. Toxic uremic waste metabolites, including urea, creatinine, and uric acid, accumulate in the body's tissues which can result in a person's death if the filtration function of the kidney is not replaced.

Dialysis is commonly used to replace kidney function by removing these waste toxins and excess water. In one type of dialysis treatment—hemodialysis—toxins are filtered from a patient's blood externally in a hemodialysis machine. Blood passes from the patient through a dialyzer separated by a semi-permeable membrane from a large volume of externally-supplied dialysis solution. The waste and toxins dialyze out of the blood through the semi-permeable membrane into the dialysis solution, which is then discarded.

Hemodialysis treatments are typically conducted at a clinic since the hemodialysis machines generally require a continuous water source, reverse osmosis machinery, and drain lines for discarding the large volumes of water and dialysis solution used during a single treatment. Hemodialysis treatment typically must be performed three or four times a week, under supervision of the clinical staff, requirements that significantly decrease a patient's autonomy and quality of life.

Certain devices reconstitute used dialysis solution from hemodialysis and/or peritoneal dialysis as opposed to discarding it. The dialysis solution can be regenerated in a machine employing a device that eliminates urea from the solution. For example, the original Redy® (REcirculating DYalysis) Sorbent System (Blumenkrantz et al., Artif Organs 3(3):230-236, 1978) includes a sorbent cartridge having five layers through which dialysis solution containing uremic waste metabolites flows in order to be regenerated.

SUMMARY

In one aspect of the invention, a dialysis system includes a device configured so that a dialysis solution can pass therethrough, a fluid line connected to the device, and a sodium control system in fluid communication with the fluid line. The device is adapted to remove one or more substances from the dialysis solution as the dialysis solution passes through the device. The fluid line is arranged so that solution exiting the device passes through the fluid line. The sodium control system is adapted to alter a sodium concentration of solution passing through the fluid line.

In another aspect of the invention, a dialysis apparatus includes a module configured to retain a device adapted to remove one or more substances from a dialysis solution as the dialysis solution passes through the device after exiting a dialysis machine. The module is configured to be releasably fluidly coupled to the dialysis machine.

In an additional aspect of the invention, a method includes removing one or more substances from spent dialysis solution by passing the spent dialysis solution through a device, and altering the sodium concentration of solution exiting the device.

In yet another aspect of the invention, a method includes removing one or more substances from spent dialysis solution by passing the spent dialysis solution through a device, and removing one or more gases from solution exiting the device.

In an additional aspect of the invention, a method includes passing a fresh dialysis solution through a dialysis machine to which a patient is connected, thereby forming a spent dialysis solution, collecting the spent dialysis solution in a container, and, after completing a treatment of the patient, removing at least some of the spent dialysis solution from the container.

In another aspect of the invention, a method includes moving a fluid from a container to a fluid line, the container being connected to the fluid line via a connection line, and detecting whether fluid is present in the connection line.

Embodiments can include one or more of the following features.

In some embodiments, the sodium control system is adapted to introduce a diluent (e.g., water) into the fluid line.

In some embodiments, the sodium control system includes a container that contains the diluent, and the sodium control system further includes a pump arranged to move the diluent from the container to the fluid line.

In some embodiments, the sodium control system is adapted to introduce sodium (e.g., a sodium chloride solution) into the fluid line.

In some embodiments, the sodium control system includes a container that contains a sodium solution, and the sodium control system is adapted to draw the sodium solution from the container to the fluid line using vacuum.

In some embodiments, the fluid line includes a venturi tube to which a line extending from the container is connected.

In some embodiments, the sodium control system includes a container that contains a sodium solution, and the sodium control system further comprises a pump arranged to move the sodium solution from the container to the fluid line.

In some embodiments, the sodium control system further includes a diluent source, and the pump is arranged to move diluent from the diluent source to the fluid line.

In some embodiments, the diluent source is a fluid line that contains pressurized diluent.

In some embodiments, the sodium control system further includes one or more valves that can be actuated to control movement of the sodium solution and the diluent to the fluid line.

In some embodiments, the sodium control system is adapted to introduce a diluent and sodium into the fluid line.

In some embodiments, the dialysis system further includes a conductivity meter that is adapted to measure conductivity of the solution passing through the fluid line, and the conductivity meter is in communication with the sodium control system.

In some embodiments, the sodium control system is adapted to alter the sodium concentration of the solution passing through the fluid line based on an output signal of the conductivity meter.

In some embodiments, the sodium control system is adapted to decrease the sodium concentration of the solution passing through the fluid line if the output signal of the conductivity meter indicates a conductivity above a predetermined conductivity.

In some embodiments, the sodium control system is adapted to increase the sodium concentration of the solution passing through the fluid line if the output signal of the conductivity meter indicates a conductivity below a predetermined conductivity.

In some embodiments, the sodium control system includes a resin containing column.

In some embodiments, the resin includes a strong acid and strong base combination.

In some embodiments, the device is a sorbent cartridge.

In some embodiments, the sorbent cartridge includes at least one layer of material capable of purifying water and/or regenerating spent dialysis solution.

In some embodiments, a layer of the sorbent cartridge comprises sodium zirconium carbonate.

In some embodiments, the dialysis system further includes a dual compartment reservoir for retaining the dialysis solution.

In some embodiments, the dual compartment reservoir includes a first reservoir for spent dialysis solution and a second reservoir for fresh dialysis solution.

In some embodiments, the first reservoir is larger than the second reservoir.

In some embodiments, the dialysis system further includes an input line and an output line. The input and output lines are in fluid communication with the second reservoir. The input line is arranged to deliver fresh dialysis solution into the second reservoir and the output line is arranged to remove fresh dialysis solution from the second reservoir.

In some embodiments, the dialysis system further includes an input/output line. The input/output line is in fluid communication with the second reservoir. The input/output line is arranged to deliver fresh dialysis solution into the second reservoir and to remove fresh dialysis solution from the second reservoir.

In some embodiments, the dialysis system further includes an infusate system in fluid communication with the fluid line. The infusate system is adapted to introduce an infusate solution into the fluid line.

In some embodiments, the infusate solution includes magnesium, calcium, and potassium.

In some embodiments, the dialysis system further includes a flow meter arranged to detect a flow rate of the dialysis solution, and the infusate system is adapted to introduce the infusate solution into the fluid line based on the flow rate of the dialysis solution.

In some embodiments, the flow meter is positioned upstream of the device.

In some embodiments, the dialysis system comprises a module fluidly coupled to a dialysis machine.

In some embodiments, the module comprises at least a portion of the sodium control system, and the device is fluidly coupled to the module.

In some embodiments, the module is electrically connected to the dialysis machine.

In some embodiments, the module is configured to retain the device.

In some embodiments, the module includes a device holder that can be arranged in a first configuration to allow fluid to pass through the device or in a second configuration to allow fluid to pass from a first portion of the device holder to a second portion of the device holder without passing through the device.

In some embodiments, the device is removed from the device holder and the first and second portions of the device holder are folded toward a back of the device holder when the device holder is in the second configuration.

In some embodiments, the dialysis machine is a hemodialysis machine.

In some embodiments, the module further includes a sodium control system that is adapted to alter the sodium concentration of the dialysis solution.

In some embodiments, the sodium control system is arranged to alter the sodium concentration of the dialysis solution after the dialysis solution passes through the device.

In some embodiments, the module further includes an infusate system that is adapted to introduce an infusate solution into the dialysis solution.

In some embodiments, the infusate solution comprises magnesium, calcium, and potassium.

In some embodiments, the infusate system is arranged to introduce the infusate solution into the dialysis solution after the dialysis solution passes through the device.

In some embodiments, the infusate system includes a container that contains an infusate solution, and the infusate system is adapted to draw the infusate solution from the container to the fluid line using vacuum.

In some embodiments, the fluid line includes a venturi tube to which a line extending from the container is connected.

In some embodiments, the module includes a pump adapted to move the dialysis solution from the module to the dialysis machine when the module is fluidly coupled to the dialysis machine.

In some embodiments, the module can be releasably fluidly coupled to any of a plurality of different dialysis machines.

In some embodiments, the module can be releasably electrically connected to any of the plurality of different dialysis machines.

In some embodiments, the method further includes passing the solution exiting the device through a dialysis machine after altering the sodium concentration of the solution exiting the device.

In some embodiments, the device is fluidly coupled to a module that is releasably fluidly coupled to a dialysis machine.

In some embodiments, the method further includes moving the spent dialysis solution from a dialysis machine to the device.

In some embodiments, the spent dialysis solution is moved from the dialysis machine to a reservoir and then from the reservoir to the device.

In some embodiments, the method further includes introducing an infusate solution into the solution exiting the device.

In some embodiments, the method further includes detecting a flow rate of the spent dialysis solution, and the infusate solution is introduced into the solution based on the detected flow rate of the spent dialysis solution.

In some embodiments, the method further includes discarding the container after removing the spent dialysis solution.

In some embodiments, the method further includes activating an indicator (e.g., an audible indicator and/or a visual indicator) if fluid is not present in the connection line.

Embodiments can include one or more of the following advantages.

In some embodiments, the dialysis system can be used in a home environment. In particular, because the sorbent cartridge allows preparation of dialysate from tap water and enables spent dialysis to be recycled, the dialysis system does not require access to large volumes of water or dialysis solution, or necessitate expensive reverse osmosis devices, or require special plumbing or wiring. Thus, the dialysis system makes in home use much more practical compared to certain previous systems.

In some embodiments, the dialysis system controls sodium levels in the dialysis solution. In certain embodiments, for example, the spent dialysis solution is passed through a sorbent cartridge that removes toxins from the dialysis solution and at the same time removes sodium. The dialysis system can include a device downstream from the sorbent cartridge that delivers sodium (e.g., sodium chloride (NaCl)) into the dialysis solution to maintain sodium levels within a desired range. Maintaining sodium levels in the dialysis solution within a desired range can help to reduce discomfort experienced by the patient as a result of increased or decreased sodium levels in the patient's blood.

In certain embodiments, the module includes a system adapted to deliver certain substances, such as magnesium, calcium, and potassium, into fluid exiting the sorbent cartridge to form regenerated dialysate. By providing this system in the module as opposed to the dialysis machine to which the module is connected during use, the number of electrical connections between the module and the dialysis machine can be reduced. This can reduce the likelihood of an electrical connection error.

In some embodiments, the dialysis system includes a sorbent cartridge mount that permits fluid to either pass through a sorbent cartridge disposed therein or to pass directly through the sorbent cartridge holder without passing through a sorbent cartridge. As a result, the dialysis system can run in a standard mode in which dialysate flows through the sorbent cartridge or in a different mode (e.g., a cleaning mode or a rinsing mode) in which the fluid (e.g., a cleaning solution or a rinsing solution) does not pass through the sorbent cartridge. This arrangement can permit fluid to be cycled through the dialysis system even when a sorbent cartridge is not present. Thus, this arrangement permits the user to clean and/or rinse the system by removing the sorbent cartridge and circulating a cleaning solution or rinsing solution through the dialysis system.

In some embodiments, the dialysis system can be used in either a mode in which dialysate is recycled and passed through the dialysis system multiple times or in a mode in which dialysate is disposed of after a single pass through the system. Thus, the user is provided with more options regarding the manner in which treatment is carried out.

Other aspects, features, and advantages will be apparent from the description and drawings, and from the claims.

DETAILED DESCRIPTION

This disclosure generally relates to dialysis systems and methods. The dialysis systems typically include a module that is capable of regenerating dialysis solution (e.g., dialysate) and controlling sodium levels within the dialysis solution. The module can be used alone or in conjunction with other devices that facilitate dialysis.

The methods described herein can include drawing used or spent dialysis solution from a dialysis machine into a reservoir, passing the dialysis solution through a sorbent cartridge thereby removing electrolytes and metabolic waste products from the spent dialysis solution, feeding the recycled dialysis solution back to the dialysis machine, and manipulating the sodium levels of the recycled dialysis solution to within appropriate physiological ranges.

The systems and methods described herein can advantageously eliminate the high volume of water usage, expensive and noisy reverse osmosis equipment, and the need for a drain line that occur with many known dialysis systems and methods. Thus, the systems and methods described herein can enable a hemodialysis machine to be relatively easily modified for use in a home environment without requiring the installation of special plumbing or wiring in a patient's home. In addition, the systems and methods described herein can allow levels of sodium in the dialysis solution to be maintained within substantially the same physiological range as is achieved in single-pass hemodialysis.

Figure 1:
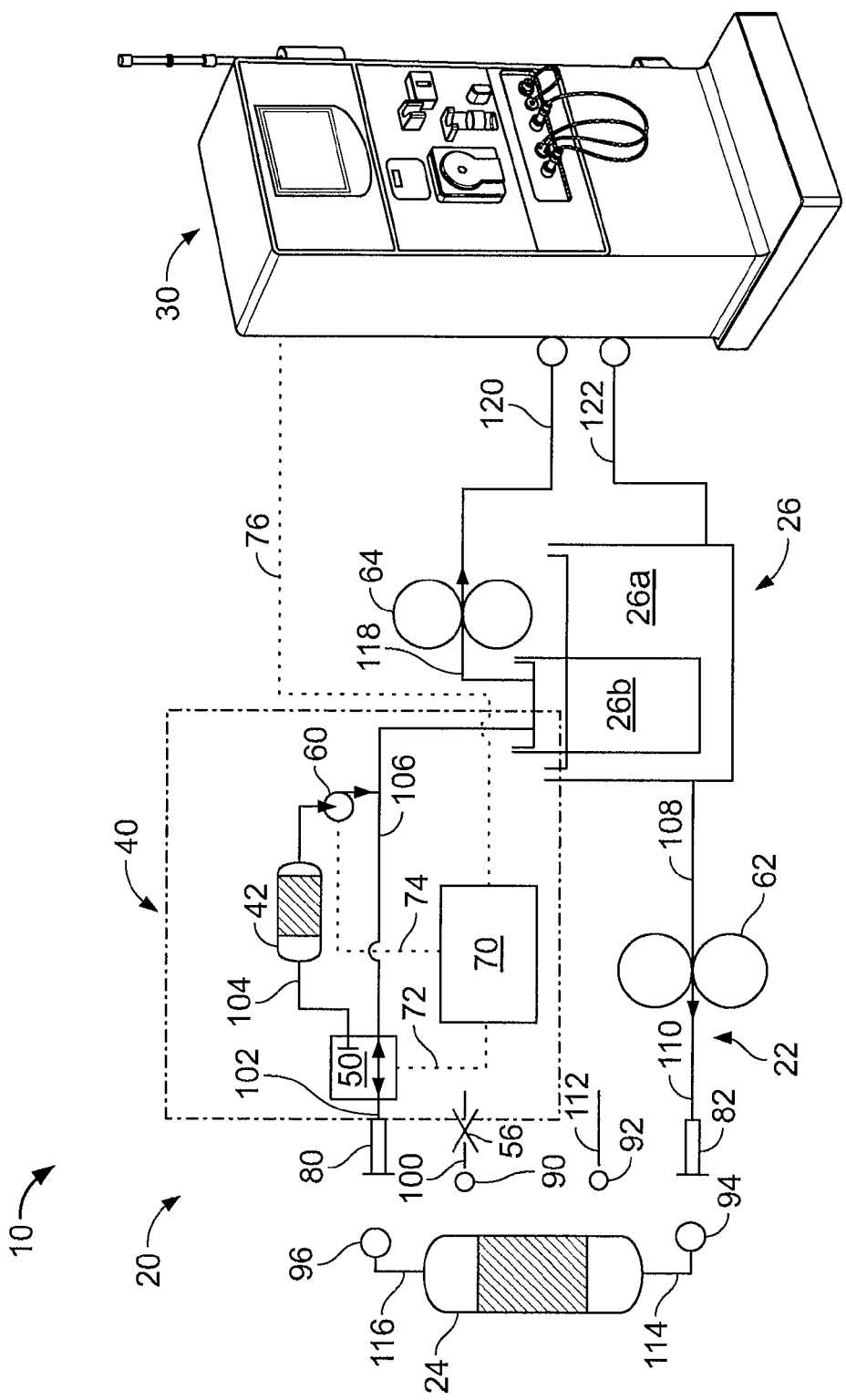
FIG. 1 is a schematic view of a module that can be used to regenerate dialysis solution and control sodium levels within the dialysis solution, and a front view of a dialysis machine.

Referring to FIG. 1, a dialysis system 10 includes a module 20 fluidly connected to a dialysis machine 30. The module 20, as discussed below, can be used to recycle dialysis solution and control sodium levels in the dialysis solution.

The module 20 generally includes a first fluid loop 22, a sorbent device 24, a reservoir assembly 26, and a system for controlling sodium 40. The sorbent device 24 and the reservoir assembly 26 of the module 20 are coupled to the first fluid loop 22 in a manner such that the sorbent device 24 and the reservoir assembly 26 are in fluid communication with the first fluid loop 22. The first fluid loop 22 includes conduits that define a flow path for circulating dialysis solution from the various components of the module 20 to the dialysis machine 30 and back to the module 20.

The sorbent device 24 includes a housing containing a sorbent cartridge capable of removing uremic toxins. In some embodiments, the cartridge is disposable. The cartridge can, for example, be constructed such that it can be disposed after use and removed from the housing. The replaced cartridge could then be replaced with a similar cartridge for a subsequent use of the module 20. The cartridge can purify water and regenerate spent dialysis solution through the use of a series of layers which can remove heavy metals (e.g., lead, mercury, arsenic, cadmium, chromium and thallium), oxidants (e.g., chlorine and chloramine), urea, phosphate and other uremic waste metabolites (e.g., creatinine and uric acid) from the solution, without removing or adsorbing excessive amounts of cations (e.g., calcium, magnesium, sodium, potassium) or essential ions.

In some embodiments, the components of the cartridge that perform the afore-mentioned functions include a purification layer that includes activated carbon; an ion exchange layer that includes a polymer phosphate binder or an ion exchange sorbent; and a urea removal layer that includes strong acid cation exchange resin and basic resin(s) or urea-degrading enzymes and an ion exchange sorbent together with a composition that rejects cations (e.g., flat membrane/hollow fibers described further herein, an ion-exchange membrane, or an encapsulation surrounding the urea removal components).

In certain embodiments, the cartridge includes the following layers and materials: sodium zirconium carbonate or other alkali metal-Group IV metal-carbonate; zirconium phosphate or other ammonia adsorbents; alumina or other like material; alumina supported urease or other immobilized enzyme layer or other material to convert urea to ammonia, such as diatomaceous earth or zirconium oxide; and granular activated carbon, such as charcoal, or other adsorbent. The sodium zirconium carbonate component can act as a phosphate adsorbent. The zirconium oxide can be capable of acting as a counter ion or ion exchanger to remove phosphate, and can be in the form of hydrous zirconium oxide (e.g., hydrous zirconium oxide containing acetate). The zirconium oxide can also be blended with the sodium zirconium carbonate when positioned in the cartridge.

Non-limiting examples of urea-degrading enzymes that can be employed in either embodiment of the sorbent cartridge include enzymes that are naturally occurring (e.g. urease from jack beans, other seeds or bacteria), produced by recombinant technology (e.g., in bacterial, fungal, insect or mammalian cells that express and/or secrete urea-degrading enzymes) or produced synthetically (e.g., synthesized). In some embodiments, the enzyme is urease.

In certain embodiments, the sorbent cartridge further includes hollow fibers. The hollow fibers can reject positively charged ions, as well as increase the capacity of the cartridge. The hollow fibers can be coated with an ion-rejecting material, which through a water-purification like mechanism allows the urea through but rejects positively charged ions such as calcium and magnesium. The material coating the hollow fibers can be any such material known to one of skill in the art (e.g., fatty acids or polymer chains like polysulfone) that can effectively reject calcium and magnesium and therefore retain the ions in the dialysis solution. Generally, to have this effect the material itself would be positively charged. In some embodiments, for example, the material used to coat the hollow fibers is cellulose acetate (e.g., cellulose triacetate). The hollow fibers that are to be coated are commercially available (e.g., Fresenius Medical Care North America) and can be coated with any desired ion-rejecting material available to one having skill in the art.

Alternatively, the hollow fibers can include an ion-selective nanofiltration membrane. Such membranes are commercially available from a number of sources (e.g., Amerida, Koch, GE, Hoechst and Dow Chemical). These membranes have pores sizes that prevent ionic substances from diffusing through the membrane. For example, there are nanofiltration membranes that have an ability to reject ions with more than one negative charge (e.g., sulfate and phosphate) while allowing single-charged ions to pass through, with the converse also being the case. In either case, the hollow fiber devices are available in a variety of dimensions and need only be small enough to fit in the replaceable cartridge, which can be sized for use in an in-home system.

In certain embodiments, the sorbent cartridge can further include a flat membrane that is covered with a positively charged material like those described above. In addition, the membrane can be an ion exchange (e.g., anion) membrane that limits the passage of positively charged ions (e.g., Astrom® Neosepta® AFX anion exchange membrane, PCA GmbH PC-SA anion exchange membrane). Advantageously, this ion exchange membrane also has an ability to adsorb phosphate.

The cartridge and/or its components or layers can be replaced (e.g., membrane, urea-degrading enzyme), regenerated (e.g., resin, sorbent) and/or sterilized for re-use when necessary (e.g., saturation, damage, depletion). In addition, the entire cartridge can be replaceable and thus removed from the dialysis system when there is a decrease in the regeneration efficiency of the cartridge (e.g., through layer saturation) or the cartridge becomes worn or damaged, for instance.

Further examples of sorbent cartridges are described in U.S. Pat. No. 6,878,283; U.S. Pat. No. 7,033,498; and in Sorb's REDY cartridge (e.g., see "Sorbent Dialysis Primer" COBE Renal Care, Inc. Sep. 4, 1993 Edition, and "Rx Guide to Custom Dialysis" COBE Renal Care Inc. Revision E. September 1993), all incorporated in their entirety by reference herein.

Figure 2:
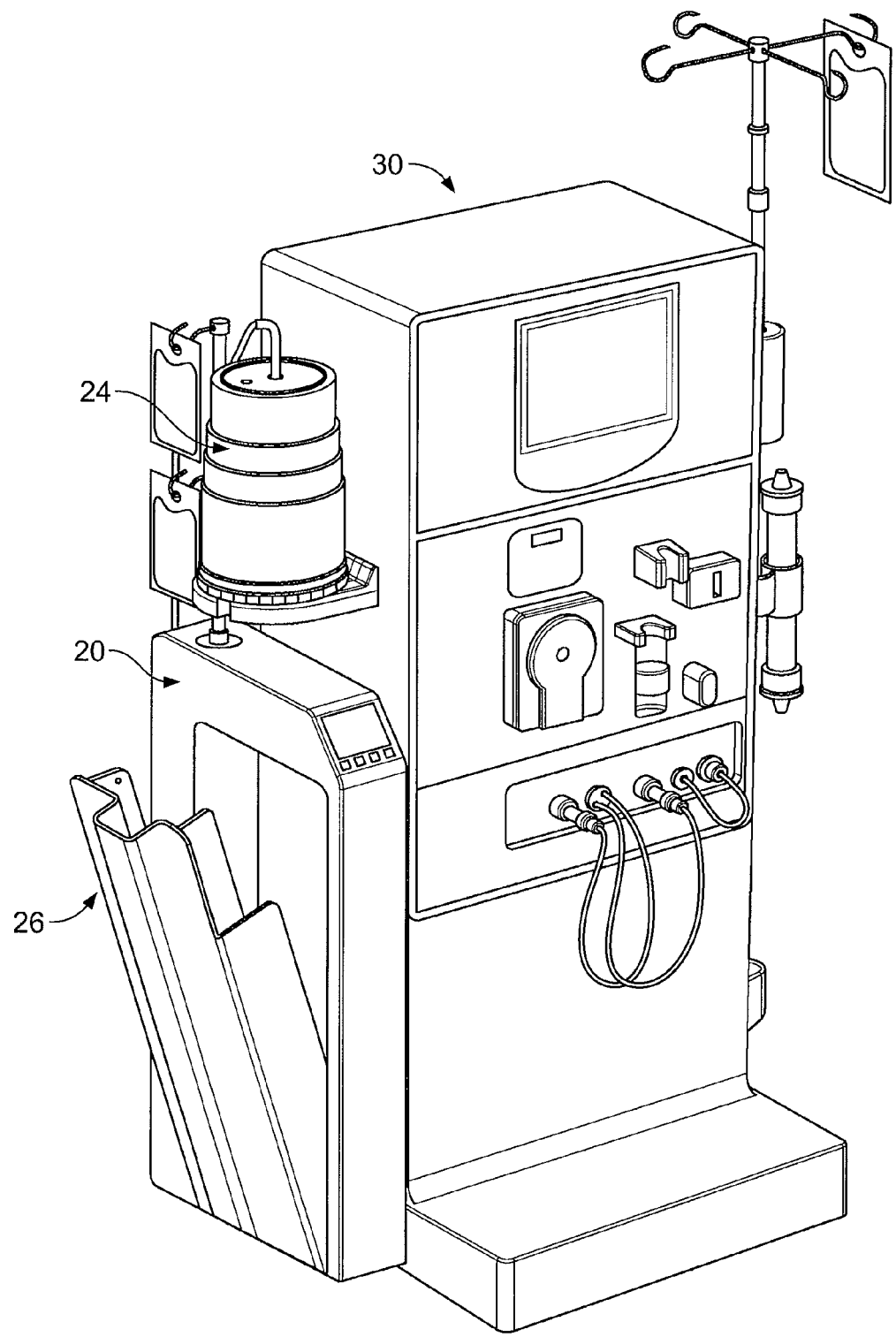
FIG. 2 is a front view of a hemodialysis machine with the module schematically illustrated in FIG. 1 coupled thereto.

The reservoir assembly 26 of the module 20 is capable of retaining dialysis solution. In some embodiments, as illustrated in FIG. 1, the reservoir assembly 26 includes a first, or spent, reservoir 26a and a second, or fresh, reservoir 26b. The first and second reservoirs can be any size or shape sufficient to accommodate and contain an initial volume of fluid and any fluid accumulation that would occur during the course of a dialysis treatment. The reservoirs can be constructed from rigid or flexible materials. The reservoirs can also be formed as an open container, or alternatively, the reservoirs can be formed as a closed container. If the reservoirs are a closed container, the container can include an opening, such as a vent, to allow for air to be expelled as fluid enters the reservoir. In some embodiments, the second reservoir 26b has a fluid volume capacity that is less than the fluid volume capacity of the first reservoir 26a. The second reservoir 26b can further be appropriately sized so as to fit within the interior of the first reservoir 26a. The first and second reservoirs 26a, 26b can be arranged and positioned relative to one another such that when the fluid capacity of the second reservoir 26b is reached, excess fluid can overflow into the first reservoir 26a. The reservoirs 26a, 26b can be fixably mated to a dialysis machine. Alternatively, the reservoirs can be removably attached to the dialysis machine. The reservoirs can be positioned at any angle on a dialysis machine. As illustrated in FIG. 2, in certain embodiments, the reservoirs 26a, 26b of the reservoir assembly 26 are positioned within a housing of the module 20 on the side of a hemodialysis machine 30.

The module 20 can further include a system for controlling an electrolyte, such as sodium. As shown in FIG. 1, a system for controlling sodium 40 includes a third, or dilution, reservoir 42 that is fluidly coupled to the first fluid loop 22. Similar to the first and second reservoirs 26a, 26b, the dilution reservoir 42 can be formed from rigid or flexible materials. The dilution reservoir can be of any size or shape that enables the reservoir to retain a volume of fluid that is sufficient to provide dilution of the fluid circulating through the components of the system. Typically, the diluent contained in the dilution reservoir 42 is water. However, any of various other suitable diluents can be used.

The system for controlling sodium 40 further includes a three-way valve 50 fluidly coupled to the first fluid loop 22 and to the dilution reservoir 42. The three-way valve 50 can be arranged to direct fluid exiting the sorbent cartridge 24 into the dilution reservoir 42 when it is desired to fill the dilution reservoir 42 and can be arranged to direct the fluid exiting the sorbent cartridge 24 to the fresh reservoir 26b once the dilution reservoir 42 has been filled, as discussed below.

The module 20 can further include a meter capable of measuring electrolyte concentration, such as measuring the sodium ion concentration in solution. For example, the meter can be a conductivity meter or a pH meter. In certain embodiments, the module includes an ammonia and/or ammonium ion monitoring device to detect ammonia molecules and/or ammonium ions in the dialysate fluid. Detection of ammonia molecules and/or ammonium ions can inhibit (e.g., prevent) ammonia and/or ammonium ions from being introduced into a patient who is undergoing treatment with the module. Additionally, the detection of ammonia and/or ammonium ions allows for monitoring the efficiency of the sorbent cartridge of the module, as well as indicating that the sorbent cartridge is properly operating. The module can also include, for example, various valves for starting and stopping fluid flow, fluid pumps or other fluid flow generating devices, flow meters for detecting flow and measuring flow rates, a dialysate fluid heater for controlling the temperature of the dialysate, and other known devices that may take part in the performance of a dialysis treatment.

Still referring to FIG. 1, to control the components (e.g., the valves, pumps, etc.) of the module, a microprocessor 70 is in electrical communication with the components of the module. The microprocessor 70 can control, alter and adjust the pump flow rates and the timing and sequencing of the components of the module in response to pre-programmed instructions or according to the patient's needs as determined by the skilled clinician. One skilled in the art would understand that the module and/or dialysis system can further include appropriate software for operating and controlling the systems and devices described herein.

The module is coupled to a hemodialysis machine 30, such as a version of the Fresenius Medical Care 2008K design. In hemodialysis, blood flows through an arterial channel to an arterial pressure sensor. The arterial pressure sensor includes a transducer so that the pressure of the blood flowing through the circuit on the arterial side can be monitored. The blood then flows through a portion of the channel that abuts a pump, such as a peristaltic pump. The pump forces the blood through the circuit. The blood then flows to the dialyzer and then to a venous pressure sensor. The access ports through which blood is removed and returned can be at a convenient and appropriate place on a patient and can be connected to the hemodialysis machine by any appropriate medical tubing.

While the arterial pressure sensor has been described as being positioned before the pump, in some embodiments, the arterial pressure sensor is after the pump. In certain embodiments, pressure sensors are positioned both before and after the blood pump.

The dialysis systems described herein can offer advantages such as enabling higher dialysate flow rates (approximately 500 ml/min). The dialysate flow rate can thus be similar to standard hemodialysis, thereby providing better clearance and allowing for only 3-4 dialysis treatments a week compared with current home hemodialysis machines that require 6 or more treatments per week. A further advantage of the dialysis system is that it allows for the module and the dialysis machine to operate at different pressures thereby inhibiting the sorbent cartridge from deforming or bursting, and the dialysis machine from air-locking. Additionally, the dialysis system uses significantly reduced volumes of fresh dialysate as compared to single pass dialysis. For example, a volume of six liters of tap water can be sufficient for the module and the dialysis system to provide fresh dialysis solution for a complete dialysis treatment.

Referring to FIG. 1, a method of operation of the dialysis system will now be described. At the initial stage of startup (if a water supply and drain are utilized), connector 80 is inserted into the connector receptacle 90, which is connected to a water source (e.g., a water tap) via a fluid conduit 100, and connector 82 is inserted into the connector receptacle 92, which is connected to a drain or waste bag via a fluid conduit 112. The sorbent cartridge 24 is not connected to the first fluid loop 22 at this time.

An inlet valve 56 is then opened to allow tap water to enter the system via the fluid conduit 100 through the inlet valve 56, continuing through the receptacle 90 and connector 80 into a fluid conduit 102. At the same time, the three-way valve 50 is turned off to allow the tap water to continue through the valve 50 to a fluid conduit 106 and into the reservoir 26b. The inlet valve 56 is kept open until an appropriate volume of tap water has entered the system. The incoming water volume can, for example, be sensed via commercially available devices such as a float switch or scale that could be connected to the electronics 70 for monitoring. Alternately, the patient can pour tap water into the system through an opening to the fresh reservoir 26b, eliminating the need for the inlet valve 56 and associated monitoring devices. In some embodiments, about six liters of tap water is introduced into the system. Alternatively, a volume of eight to nine liters of tap water may be used for certain patients.

Once the system has been initially primed, the patient fluidly connects the sorbent cartridge 24 to the fluid loop 22 by removing connector 80 from receptacle 90 and inserting connector 80 into the sorbent cartridge at receptacle 96 and by removing connector 82 from receptacle 92 and inserting connector 82 into receptacle 94. With connectors 80 and 82 inserted into receptacles 96 and 94, respectively, fluid circulating through the fluid loop 22 can pass through the sorbent cartridge 24.

Beginning at the spent dialysate reservoir 26a, fluid exits the bottom of the spent dialysate reservoir 26a through a fluid conduit 108, entering a recirculation pump 62 that moves the fluid through a fluid conduit 110 and into the bottom of the sorbent cartridge 24 via a fluid conduit 114. The fluid passes through the sorbent cartridge 24 and exits the top of the sorbent cartridge 24 via a fluid conduit 116 through the receptacle 96 and the connector 80, and enters the fluid conduit 102.

The three-way valve 50 is energized by the electronics 70 via a control line 72 to allow the processed fluid to enter the dilution reservoir 42 via a fluid conduit 104. The infusion pump 60 is turned off at this time, allowing the fluid to fill the dilution reservoir 42. This volume of sodium free fluid can be used later in the treatment to dilute the overall sodium content of the dialysis solution circulating in the dialysis system.

Once the dilution reservoir 42 is filled, valve 50 is turned off causing the remaining fluid from the spent reservoir 26a and the sorbent cartridge 24 to pass through a fluid conduit 106 and into the fresh reservoir 26b. At this stage, the fluid is delivered from the fresh reservoir 26b to the dialysis machine 30 where it is spiked with a known concentrate (either liquid or powder form) to attain a base sodium and bicarbonate level. This spiking process can be carried out manually or automatically. At this time, as described above, fluid continues to recirculate through the dialysis machine 30 and the module 20.

The fluid is pulled from the fresh reservoir 26b into the dialysis machine 30 through a fluid conduit 118 by a pressure pump 64 that can be adjusted to sufficiently feed the dialysis machine 30 via a fluid conduit 120. Within the dialysis machine 30, acid containing magnesium, calcium, potassium, dextrose and other desired constituents, is proportioned along with a known quantity of water to adjust the electrolyte levels of the fluid to levels specified by the physician. During treatment, sodium levels in the sorbent cartridge 24 tend to build so that sodium levels increase in fluid passing through the sorbent cartridge 24. The additional volume of water from the acid concentrate can contribute to the dilution of the sodium levels generated by the sorbent cartridge 24 and increase the water levels in the spent reservoir 26a. The spent dialysate exits the hemodialysis machine 30 through a drain line connected to a fluid conduit 122 and travels into the spent reservoir 26a.

The spent dialysate is drawn from the spent reservoir 26a to the sorbent cartridge 24 by pump 62. As a result of being passed through the sorbent cartridge 24, toxins, such as urea, and certain dialysate components, such as magnesium, calcium, and potassium are stripped from the spent dialysate. The recycled dialysate exiting the sorbent cartridge 24 is then transferred to the fresh reservoir 26b and ultimately is cycled back through the dialysis machine 30.

During the treatment, a signal transmitted from the dialysis machine 30 is monitored by the microprocessor 70 via a control line 76 for conductivity of the recycled dialysate going to the patient. Since the Ca, Mg and K are volumetrically proportioned, and added to Ca-free, Mg-free, and K-free solution exiting from the sorbent cartridge 24, any changes to the base conductivity would generally be a result of sodium generation coming from the sorbent cartridge 24. If the sodium content exceeds a specified level setting that has been entered into software in communication with the microprocessor 70, the microprocessor 70 transmits a signal to the infusion pump 60 via another control line 74 to activate the infusion pump 60, allowing further dilution of the sodium in the reservoir volumes with the sodium free solution that was collected in the dilution reservoir 42 prior to treatment. An alternate control method would be to monitor the conductivity at the drain line of the hemodialysis machine 30 feeding the module 20, eliminating the need for an electronic signal from the hemodialysis machine 30 to the module 20.

An alternative embodiment to the dilution method would be to have a receptacle at the dilution reservoir 42 where a male connector of the dialysis machine can plug into the dilution reservoir 42 and the dialysis machine 30 could proportion sodium free fluid into the system using microprocessors of the dialysis machine, thereby eliminating the need for an infusion pump 60.

Another embodiment to the dilution method would be to utilize packaged sodium-free water that can be proportioned through a pump in the dialysis machine 30 as a diluent, thereby eliminating the need for valve 50, dilution reservoir 42 and infusion pump 60.

The control method for the dilution system can alternatively or additionally be via electronic feedback from the hemodialysis machine, a separate conductivity probe, or a timed sequence.

Upon completion of treatment, the patient would disconnect the sorbent cartridge 24 and re-insert connector 80 into receptacle 90 and connector 82 into receptacle 92. At this time pump 62 could empty the reservoirs 26a, 26b if the drain line was utilized bringing the system back to an empty state until the next treatment. Alternatively, the drain line could be eliminated by having the patient manually drain the reservoirs at the completion of the treatment.

After draining the reservoirs 26a, 26b, the module and dialysis machine could be cleaned by circulating a cleaning solution, such as bleach, through the fluid loop 22 of the module, into and through the dialysis machine 30, and back to the module 20. Disinfection of the dialysis system can alternatively or additionally include heat disinfection techniques.

While certain embodiments have been described, other embodiments are possible.

Figure 3:
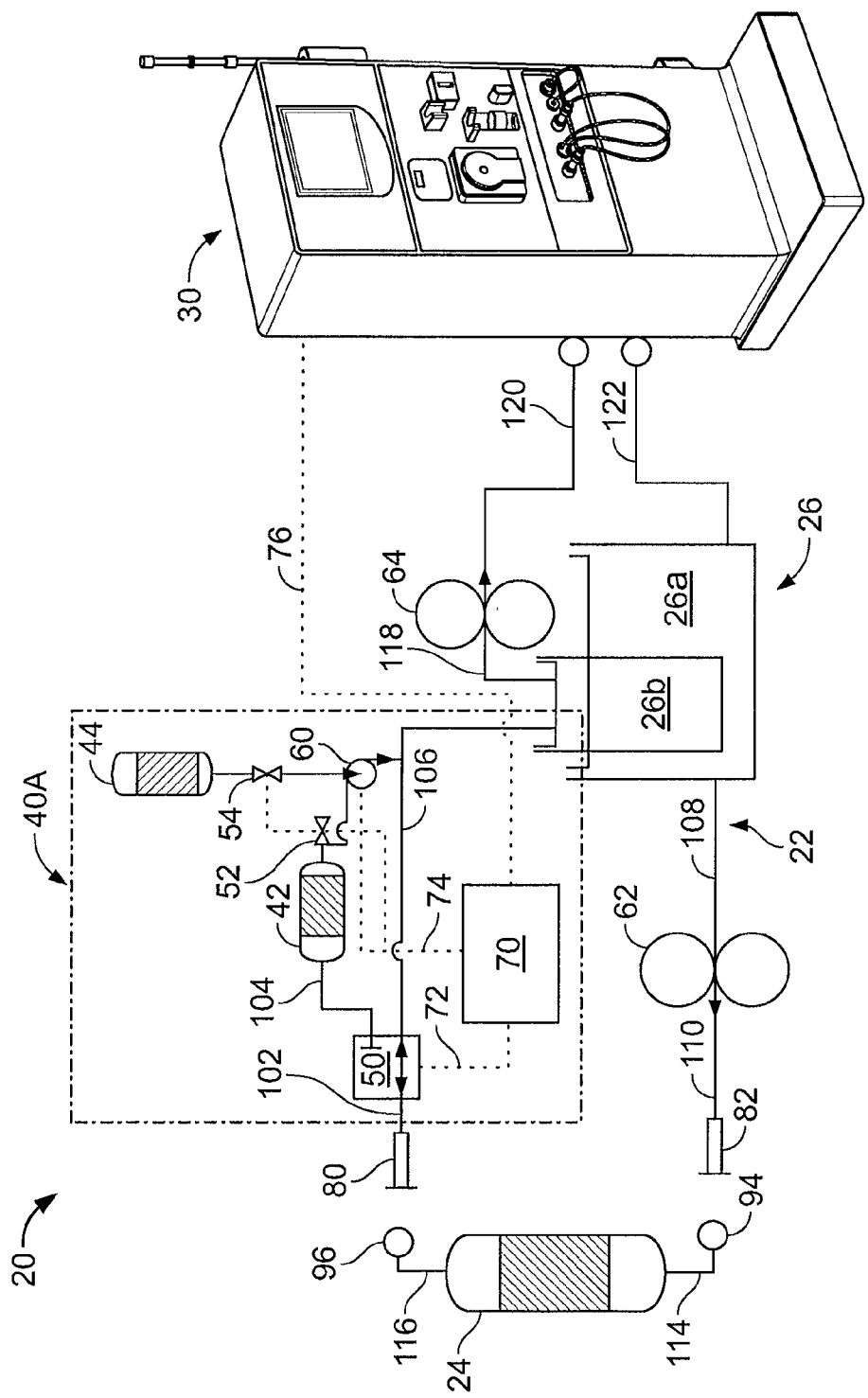
FIG. 3 is another schematic view of a module that can be used to regenerate dialysis solution and control sodium levels within the dialysis solution, and a front view of a dialysis machine.

For example, while the system for controlling sodium 40 has been described as being adapted to decrease sodium levels in the fluid passing through the system, the system for controlling sodium can alternatively or additionally be adapted to increase sodium levels in the fluid passing through the system. As shown in FIG. 3, for example, a system for controlling sodium 40A includes a container 44 containing sodium concentrate solution in addition to the dilution reservoir 42. An on-off flow switch or valve 52 is positioned between the dilution reservoir 42 and the flow pump 60, and an on-off flow switch or valve 54 is positioned between the sodium concentrate container 44 and the flow pump 60. The flow pump 60 can serve to infuse the sodium concentration solution or the dilution volume into the first fluid loop 22 depending on the state of the valves 52 and 54. If it is determined that the fluid exiting the sorbent cartridge 24 has excessively high levels of sodium, which can occur as sodium levels build up within the sorbent cartridge 24, then valve 52 is opened, valve 54 is closed, and pump 60 is activated to draw dilution water into the fluid conduit 106. If, on the other hand, the sodium levels in the fluid exiting the sorbent cartridge 24 are too low, which can occur in the initial stages of treatment as the fresh sorbent cartridge 24 strips sodium from the fluid passing therethrough, then valve 52 is closed, valve 54 is opened, and pump 60 is activated to draw the sodium concentrate solution into the fluid conduit 106. As described, the sodium concentrate can be used to adjust and manipulate the sodium levels in the dialysis solution and can thus be used to adjust and manipulate a patient's sodium levels.

Figure 4:
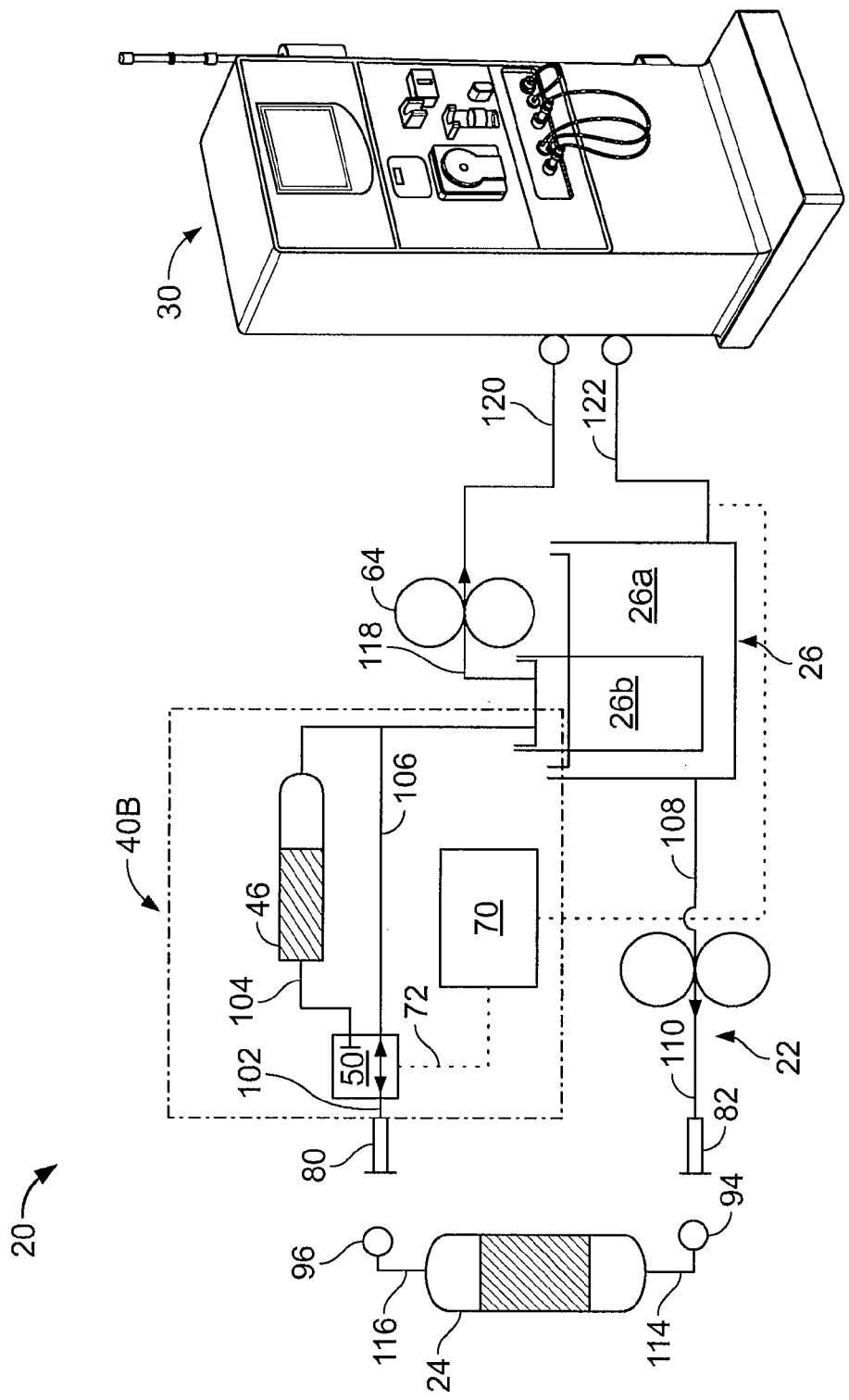
FIG. 4 is yet another schematic view of a module that can regenerate dialysis solution and control sodium levels within the dialysis solution, and a front view of a dialysis machine.

While the systems for controlling sodium have been described as including a dilution reservoir containing a diluent (e.g., tap water) that can be added to the fluid circulating through the system, other devices can alternatively or additionally be used to control sodium levels within the circulating fluid. As shown in FIG. 4, for example, in some embodiments, a system for controlling sodium 40B includes a column 46 containing a strong acid/strong base resin combination that can be used to remove sodium from the fluid circulating through the system. The column 46 can be formed from a replaceable cartridge. Alternatively, the column 46 can be formed from a deionization polisher. The strong acid/strong base resin combinations can remove sodium from the dialysis solution and control pH. In the system for controlling sodium 40, the three-way valve 50 is fluidly connected to the first fluid loop 22 and to the column 46. Upon detecting excessive sodium levels within the fluid circulating through the system, three-way valve 50 can be used to divert the effluent from the sorbent cartridge 24 through the strong acid/strong base ion exchange resin mixture in the column 46 to remove sodium in exchange for water. Advantageously, this method allows sodium levels to be adjusted without the addition of water to the fluid circulating through the system. Thus, additional reservoir volume is not required to compensate for the dilution. However, an exchange program may be used to regenerate the deionization polisher. The control method for either the dilution or the ion exchange systems could be via electronic feedback from the hemodialysis machine, a separate conductivity probe or a timed sequence.

While the dialysis machines of certain systems discussed above have been described as being adapted to add dialysis solution solutes, such as magnesium, calcium, and potassium, to the recycled dialysis solution, in some embodiments, the module includes a system for adding dialysis solution solutes into the recycled dialysis solution.

While the reservoir assembly 26 has been described as being formed by the module, in some embodiments, a separate bag (e.g., a disposable bag) is connected to the module for holding the fresh and spent dialysis solution.

In certain embodiments, the module includes a sorbent cartridge holder or mount that can be put in a first configuration in which dialysis solution can pass through a sorbent cartridge connected to the holder, or in a second configuration in which dialysis solution is directed through the mount without passing through the sorbent cartridge.

Figure 5:
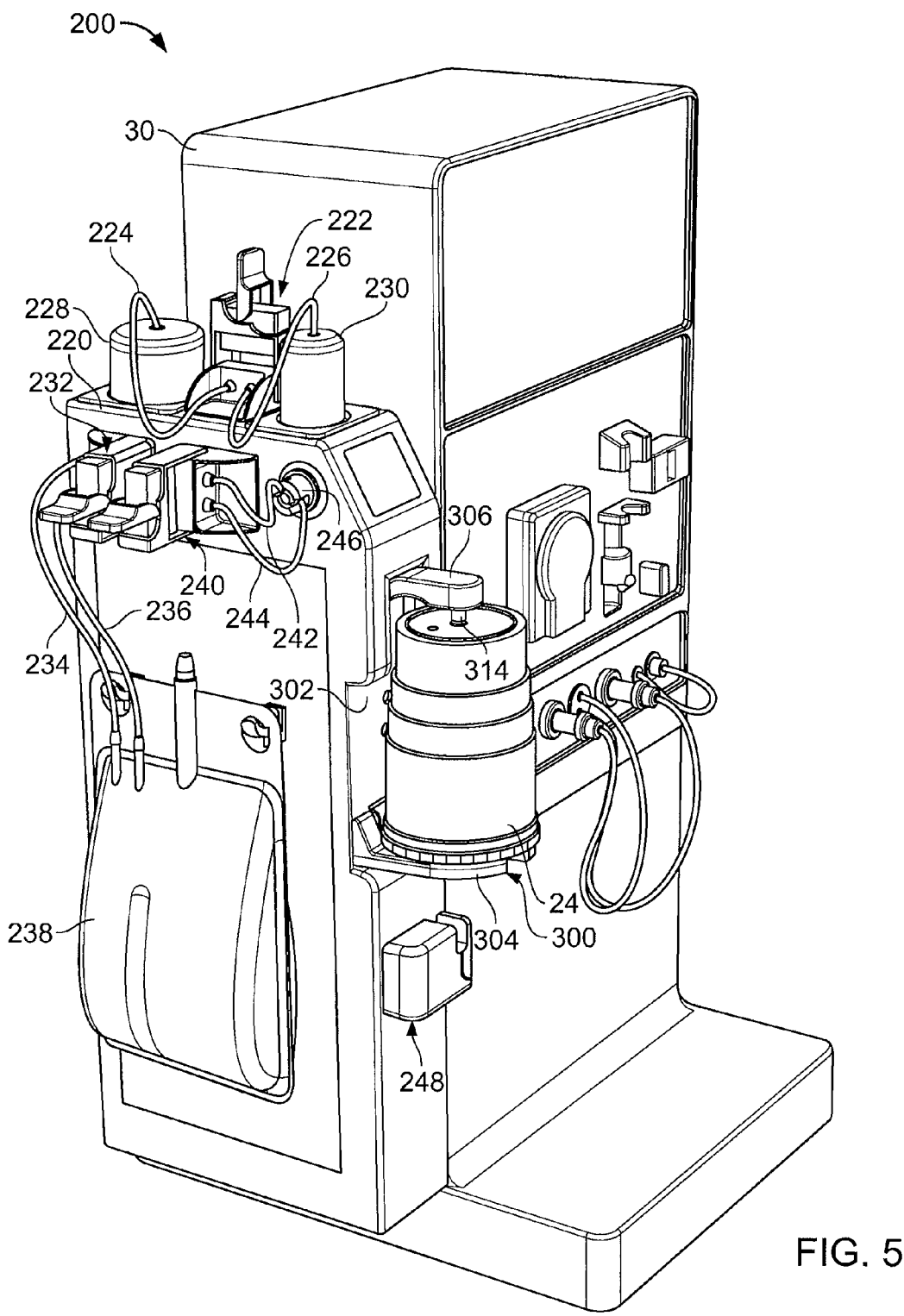
FIG. 5 is a perspective view of a dialysis system that includes a dialysis machine and a module with a sorbent cartridge holder that is holding a sorbent cartridge.

FIG. 5 shows a dialysis system 200 that includes a module 220 fluidly coupled to dialysis machine 30. The module 220 includes a sorbent cartridge holder 300 configured to hold the sorbent cartridge 24. The module 220 also includes a manifold 222 to which fluid lines 224, 226 extending from an infusate container 228 and a sodium chloride container 230 are connected, a manifold 232 to which fluid lines 234, 236 extending from a dialysate bag or reservoir 238 are connected, and a manifold 240 to which fluid lines 242, 244 extending from an ammonium ($NH_4$) sensor 246 are connected. The module 220 further includes a manifold 248 that can be used to fluidly connect other components, such as a priming solution bag, a rinsing solution bag, a cleaning solution bag, and/or a drain bag to the module 220. Each of manifolds 222, 232, 240, and 248 can, for example, include projections on which fluid lines can be positioned to connect the various components described above to their respective manifold. Any of various other suitable connection mechanisms can alternatively or additionally be used to connect the fluid lines to the manifolds.

When in an open position, as shown in FIG. 5, the manifold 222 permits an infusate solution (e.g., a solution including magnesium, calcium, and potassium) and a sodium chloride solution to be delivered into fluid circulating through the module 220. Pumps and valves within the module 220 can, for example, be activated to pump the infusate solution and sodium chloride into the fluid circulating within the module 220. Similarly, the manifold 232 allows fluid to be transferred from the module 220 to the bag 238 and vice versa. Using pumps and valves within the module 220, fluid can be pumped into and suctioned out of the bag 238 via the fluid line 234 connected to the manifold 232. The manifold 240 permits fluid to be transferred from the module 220 to the ammonium sensor 246 and vice versa. By activating pumps and valves within the module 220 in a desired manner, the fluid can be pumped from the module 220 to the ammonium sensor 246 and can be drawn back to the module 220 from the ammonium sensor. The manifold 248 can also be placed in an open configuration during use and connected to fluid lines such that by activating pumps and valves within the module, fluid can be drawn into the module 220 from a bag (e.g., a priming solution bag, a rinsing solution bag, a cleaning solution bag) and/or pumped from the module into a bag (e.g., a drain bag). With the sorbent cartridge 24 fluidly connected to the cartridge holder 300, as shown in FIG. 5, fluid circulating within the module 220 is allowed to pass through the sorbent cartridge 24.

During dialysis treatment, the module 220 is configured in the manner shown in FIG. 5 to permit fluid communication between the fluid circulating within the module 220 and the sorbent cartridge 24, the infusate container 28, the sodium chloride container 30, the dialysate bag 38, the ammonium sensor 46, and, in some cases, one or more additional bags that can be connected to the module 220 via the manifold 248.

Figure 6:
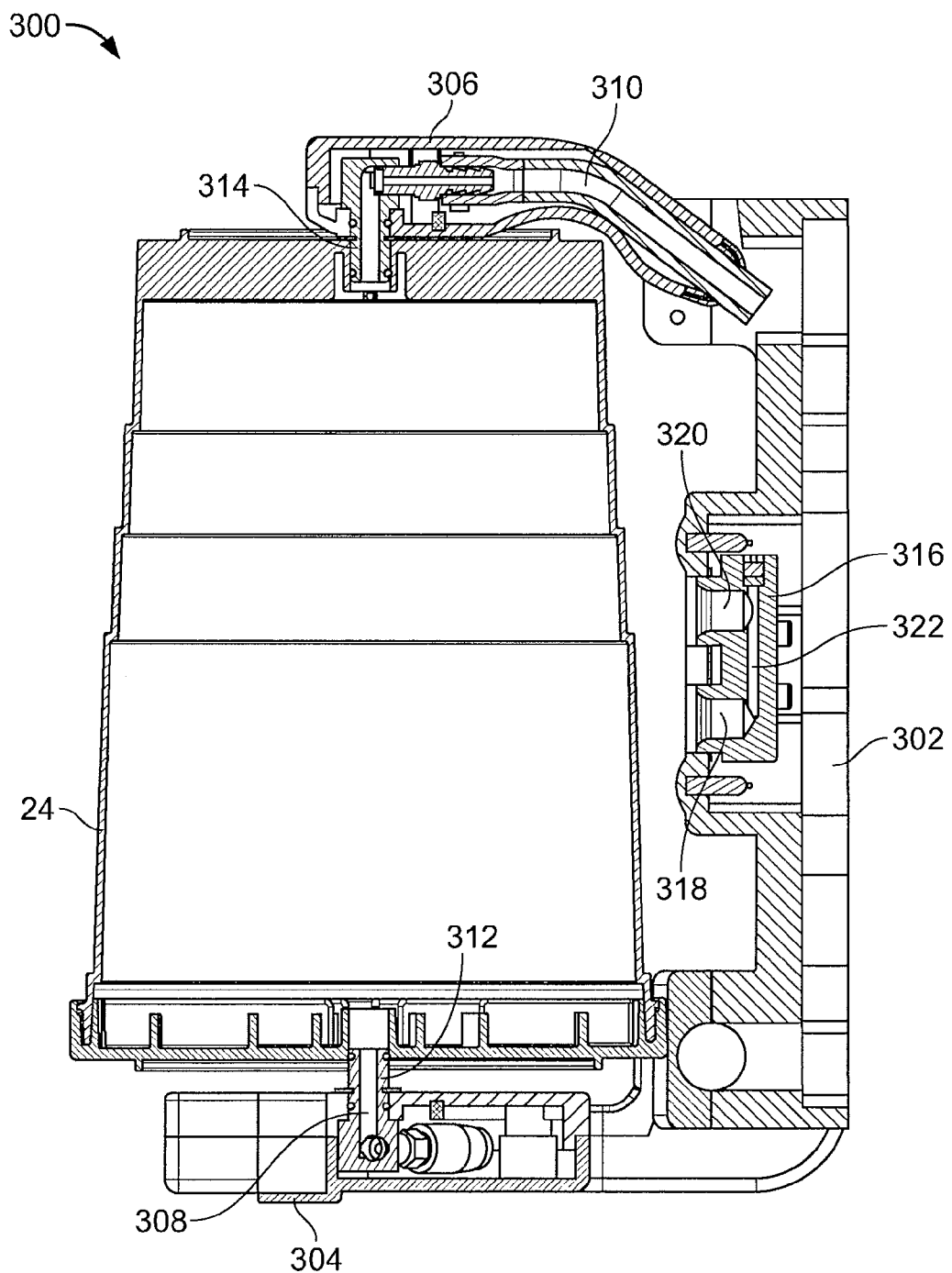
FIG. 6 is a cross-sectional view of the sorbent cartridge holder of FIG. 5 with a sorbent cartridge positioned in the sorbent cartridge holder.

FIG. 6 is a cross-sectional view of the cartridge holder 300 holding the sorbent cartridge 24. As shown in FIGS. 5 and 6, the cartridge holder 300 includes a back 302, a base 304 that is pivotably connected to a bottom portion of the back 302, and an arm 306 that is pivotably connected to a top portion of the back 302. The sorbent cartridge 24 can be positioned between and held in position by the base 304 and the arm 306. Referring to FIG. 6, fluid passageways 308, 310 extend though the base 304 and the arm 306, respectively. The base 304 and the arm 306 also include fittings (e.g., male nipples) 312, 314 that cooperate with the sorbent cartridge 24 to place the fluid passageways 308, 310 of the base 304 and the arm 306 in fluid communication with an interior chamber of the sorbent cartridge 24 and to help retain the sorbent cartridge 24 in position between the base 304 and the arm 306. This configuration permits fluid to pass through the fluid passageway 308 of the base 304 and into the interior chamber of the sorbent cartridge 24. The fluid can pass through the sorbent cartridge 24 and into the fluid passageway 310 of the arm 306. The base 304 and/or the arm 306 can be spring loaded. This can help the base 304 and the arm 306 to retain the sorbent cartridge 24 while also permitting the base 304 and the arm 306 to rotate about their hinged axes in the event that the sorbent cartridge 24 expands or contracts (e.g., in response to fluid retention and fluid pressure therein) during use. The fluid passageways 308, 310 of the base 304 and the arm 306 are connected to fluid lines within the module 220 such that the cartridge holder 300 can receive fluid (e.g., spent dialysis solution) from the module 220 and return fluid (e.g., recycled dialysis solution) to the module 220.

Referring again to FIG. 5, during dialysis, as discussed in greater detail below, spent dialysis solution is moved from the dialysis machine 30 into the module 220 where it passes through the sorbent cartridge 24, and then the recycled dialysis solution exiting the sorbent cartridge 24 is moved back to the dialysis machine 30. As the spent dialysis solution is passed through the sorbent cartridge 24, toxins, such as urea, and other substances, such as calcium, magnesium, and potassium are stripped from the spent dialysis solution. Sodium can also be stripped from the spent dialysis solution or, in certain cases, added to the spent dialysis solution as the spent dialysis solution passes through the sorbent cartridge 24. Thus, calcium, magnesium, potassium, and sodium levels of the recycled dialysis solution exiting the sorbent cartridge 24 can be altered (e.g., by introducing calcium, magnesium, potassium, sodium, and/or a diluent into the recycled dialysis solution) to restore concentrations of those substances to desired levels. As the recycled dialysis solution then passes through a dialyzer in the dialysis machine 30, toxins are transferred from the patient's blood into the dialysis solution, forming spent dialysis solution. This spent dialysis solution is then circulated through the module 220 again to recycle or regenerate the spent dialysis solution. This process can be repeated until a desired amount of toxins have been removed from the patient's blood. Because the dialysis solution is recycled during the treatment as opposed to simply being discarded, the volume of dialysis solution used during the treatment can be substantially reduced relative to certain conventional hemodialysis techniques. In addition, maintaining the concentration of the various substances within the dialysis solution, such as calcium, magnesium, potassium, and sodium, can help to prevent the patient from experiencing discomfort during the treatment.

Referring again to FIG. 6, a bypass component 316 is secured to the back 302 of the cartridge holder 300. The bypass component 316 includes ports 318 and 320 that are arranged to receive the fittings 312 and 314 of the base 304 and the arm 306 when the base 304 and the arm 306 are pivoted into engagement with the back 302 (after the sorbent cartridge 24 has been removed from the cartridge holder 300). The bypass component also includes a fluid passage 322 that extends within the back 302 and fluidly connects the ports 318, 320 to one another. The bypass component 316 allows fluid to pass through the cartridge holder 300 even when the sorbent cartridge 24 has been removed from the cartridge holder 300.

Figure 7:
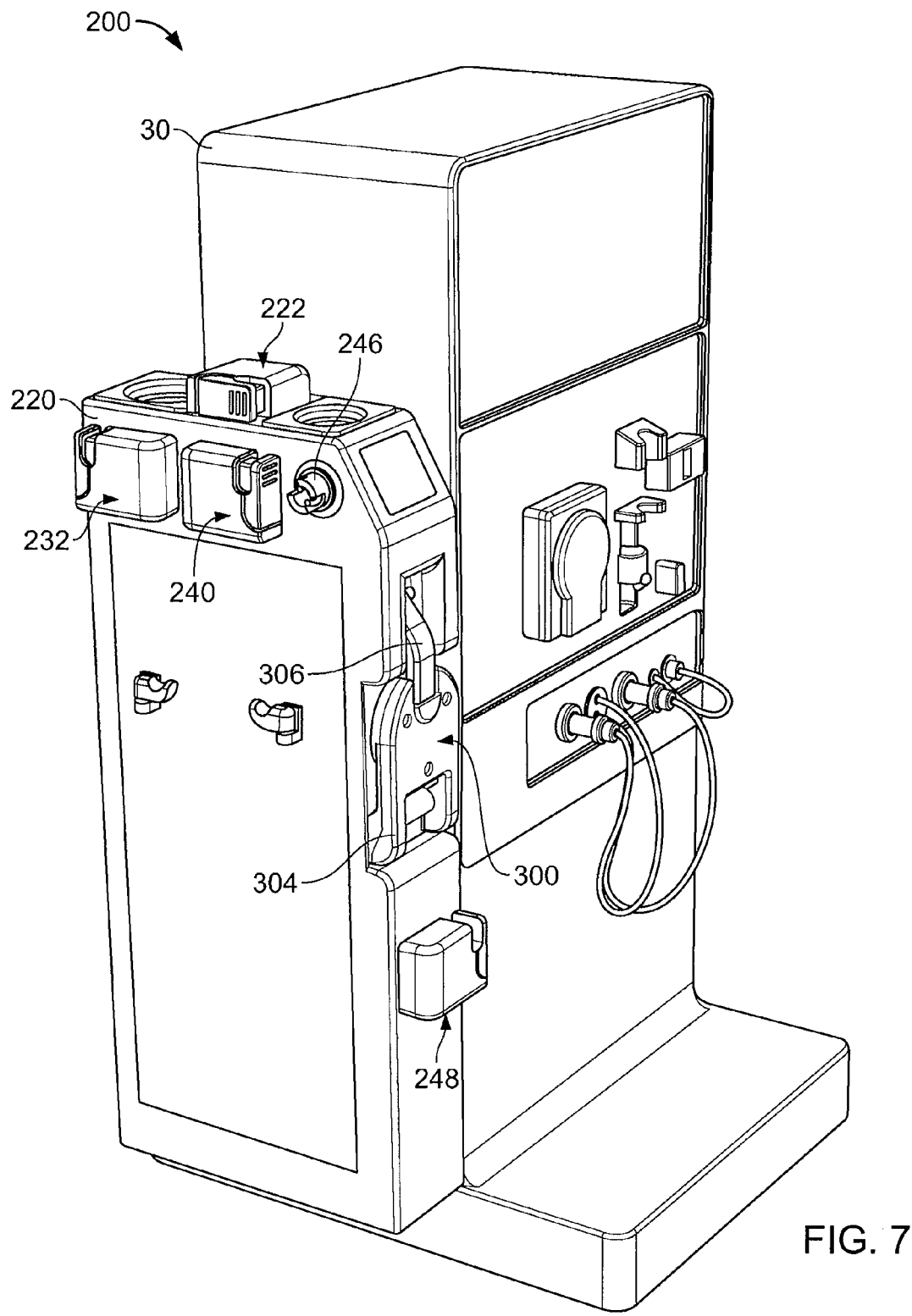
FIG. 7 is a perspective view of the dialysis system of FIG. 5, with the sorbent cartridge removed and the sorbent cartridge holder in a folded configuration.

FIG. 7 shows the system 200 with all external components (e.g., the sorbent cartridge 24, the infusate container 228, the sodium chloride container 230, the bag 238, and their associated fluid lines) disconnected from the module 220 and with the manifolds 222, 232, 240, and 248 and the sorbent cartridge holder 300 in a closed position. When the manifolds 222, 232, 240, and 248 and the sorbent cartridge holder 300 are in their closed positions, they inhibit (e.g., prevent) fluid from exiting the module 220, and thus permit fluid (e.g., a cleaning solution or a rinsing solution) to be circulated in a closed circuit within the module 220 and the dialysis machine 30. Each of the manifolds can, for example, include a member that abuts or extends into fluid line connection ports of the manifolds when the manifolds are in the closed position to create a fluid-tight seal.

Figure 8:
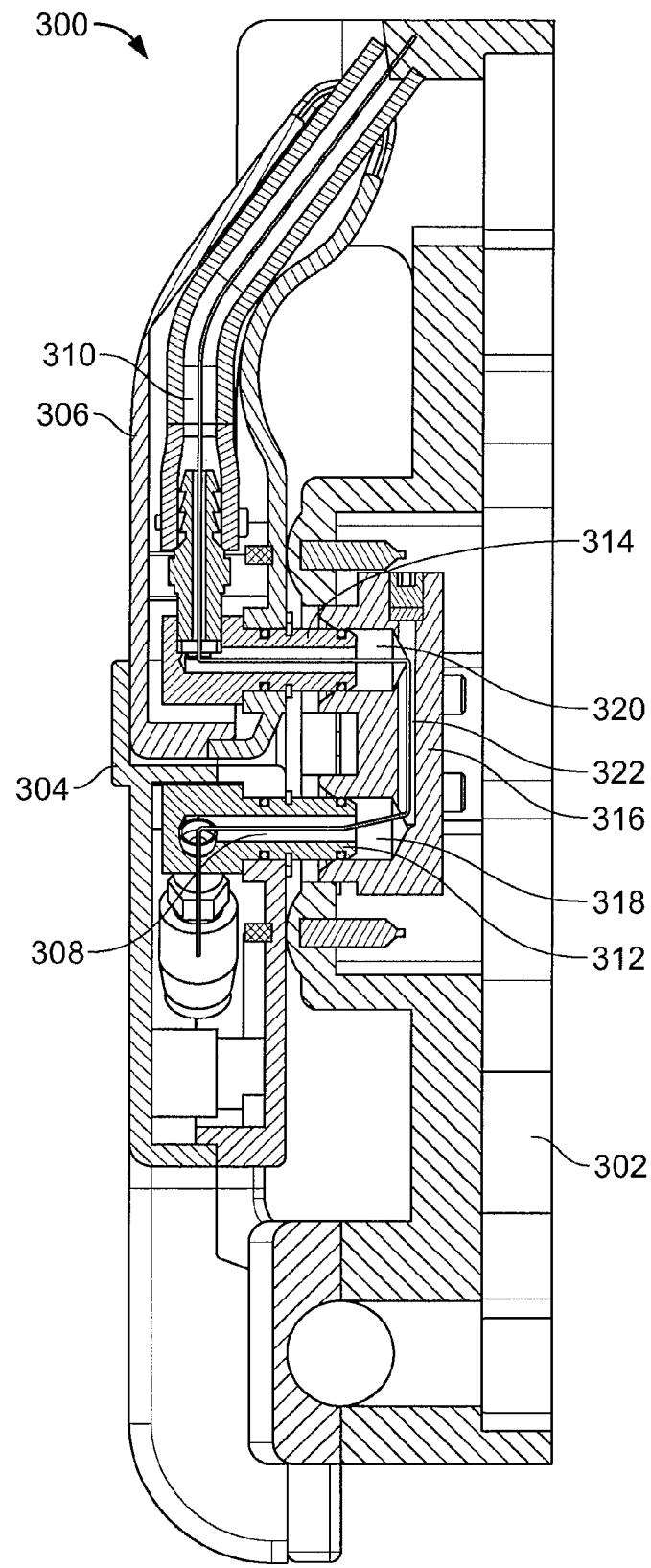
FIG. 8 is a cross-sectional view of the sorbent cartridge holder of FIG. 5 with the sorbent cartridge removed and the sorbent cartridge holder in a folded configuration.

FIG. 8 is a cross-sectional view of the cartridge holder 300 in its folded or closed configuration. Referring to FIGS. 7 and 8, in this folded configuration, the base 304 and the arm 306 are pivoted toward the back 302 and the fittings 312, 314 are disposed in the ports 318 and 320 of the bypass component 316. This configuration permits fluid to pass through the fluid passageway 308 of the base 304 and into a fluid passageway 322 extending through the bypass component 316. The fluid then passes from the fluid passageway 322 of the bypass component 316 to the fluid passageway 310 of the arm 306. Thus, even when the sorbent cartridge 24 has been removed from the cartridge holder 300, a fluid stream can be maintained through the cartridge holder 300.

The external components (e.g., the sorbent cartridge 24, the infusate container 228, the sodium chloride container 230, the bag 238, and their associated fluid lines) are constructed as disposable, single use components and can thus be disconnected from the module 220 and discarded after completion of dialysis treatment. The manifolds and the sorbent cartridge holder 300 can then be closed and a cleaning and/or rinsing solution can be circulated through the module 220 and the dialysis machine 30 to prepare the module 220 and the dialysis machine 30 for a subsequent use.

Figure 9:
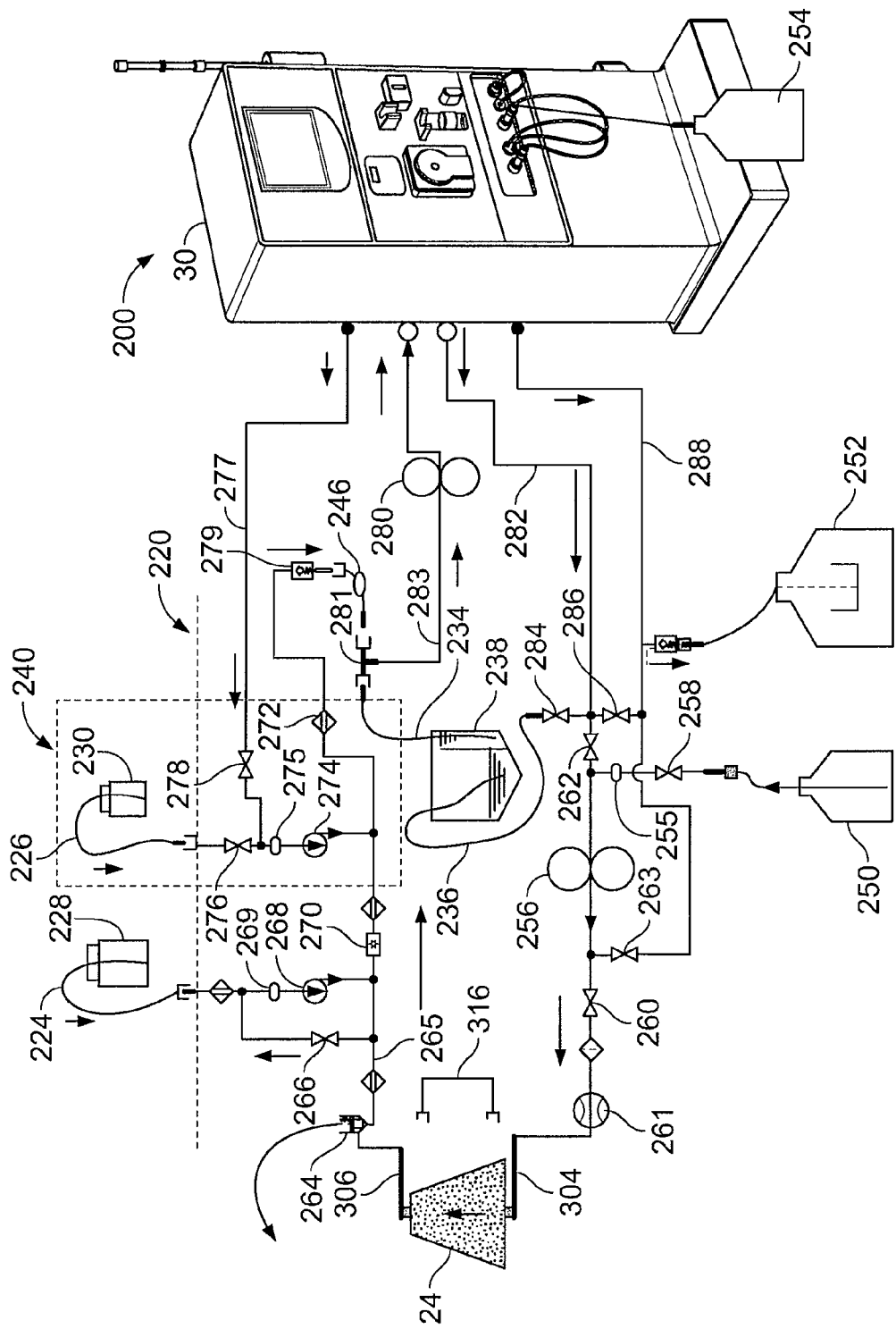
FIG. 9 is a schematic view of the module of FIG. 5, and a front view of the dialysis machine of FIG. 5.

FIG. 9 is a schematic view of the module 220 coupled to the dialysis machine 30. As shown in FIG. 9, in addition to the external components that have been described as being connected to the module 220, a dialysate bag 250 and a drain bag 252 are also connected to the module 220 via the manifold 248 (shown in FIGS. 5 and 7). In addition, a dilution bag 254 is fluidly connected to the dialysis machine 30.

Still referring to FIG. 9, a method of performing hemodialysis will now be described. Prior to beginning the dialysis treatment, dialysate is drawn from the dialysate bag 250, passed through the sorbent cartridge 24, and routed to the bag 238. This can be done by activating pump 256 with valves 258, 260 opened and valve 262 closed. After exiting the bag 250 and passing through the valve 258, the dialysate passes through a fluid detector 255, which is adapted to detect the presence or absence of fluid within the line. Fluid detectors of this type are available, for example, from Introtek and Cosense. The dialysate is drawn from the bag 250 until the fluid detector 255 detects the absence of fluid in the line, indicating that all of the dialysate has been forced from the bag 250 into the module 220. Upon detecting the absence of fluid in the line, the fluid detector 255 can transmit this information to a control unit (e.g., microprocessor) that can cause the valves and pumps throughout the system to operate in a way to cause the dialysate to recirculate within the module 220 and/or the dialysis machine 30.

Prior to reaching the sorbent cartridge 24, the dialysate passes through a flow meter 261 that is configured to measure the flow rate of the dialysate passing therethrough. A signal representing the flow rate of the dialysate can be transmitted from the flow meter 261 to a control unit (e.g., a microprocessor). As discussed below, the detected flow rate of the dialysate can be used to control metering of the infusate into the dialysate.

As the dialysate passes through the sorbent cartridge 24, certain substances, such as calcium, magnesium, potassium, and sodium may be removed from the dialysate. As discussed above, the sorbent cartridge 24 is also adapted to remove toxins, such as urea, from fluid flowing therethrough, but the dialysate from the dialysate bag 250 would generally not contain any urea. Upon exiting the top of the sorbent cartridge 24, the dialysate flows through a bubble trap 264, which helps to ensure that gases within the dialysate are released. With valve 266 closed, the dialysate is then forced through fluid line 265. The infusate solution, which includes magnesium, calcium, and potassium, is then pumped into the fluid line 265 from the infusate solution container 228 by activating a pump 268. The combination of the dialysate and the infusate solution are mixed within a mixing chamber 270.

After exiting the mixing chamber, the dialysate continues to flow through the fluid line 265 and passes through a conductivity meter 272. The conductivity meter 272 can estimate, based on the conductivity of the fluid passing therethrough, the concentration of sodium within the fluid. A pump 274 and valves 276, 278 can then be activated in a manner to introduce sodium chloride into the fluid line 265 from the sodium chloride container 230 if the conductivity reading indicates that the sodium level in the dialysate is lower than desired or to introduce dilution water (e.g., AAMI quality water) into the fluid line 265 if the conductivity reading indicates that the sodium level in the dialysate is higher than desired. The dilution water is delivered to the dialysate passing through the fluid line 265 from the bag 254 connected to the dialysis machine 30. The dialysis machine 30 draws the dilution water from the bag 254 and delivers it to the module 220 where it passes through a fluid line 277 toward the valve 278. The dilution water can be metered into the fluid line 265 by activating the pump 274 and opening the valve 278. Similarly, the sodium chloride solution can be metered into the fluid line 265 by activating the pump 274 and opening the valve 276.

Prior to reaching the fluid line 265, the infusate solution and the sodium chloride solution pass through fluid detectors 269 and 275, which can detect the presence or absence of fluid. The fluid detectors 269, 275 can be similar in construction to the fluid detector 255 discussed above.

A microprocessor is used to control the pumps 268, 274 and the valves 276, 278. The microprocessor is connected to flow meter 261, the conductivity meter 272, the pumps 268, 274, and the valves 276, 278. The measured flow rate of the dialysate is transmitted in the form of a signal from the flow meter 261 to the microprocessor. The microprocessor controls the pump 268 as a function of the flow rate of the dialysate measured by the flow meter 261. This arrangement helps to ensure that a desired amount of the infusate is added to the dialysate, and thus helps to ensure a desired proportion of the infusate to the dialysate. The conductivity reading is similarly sent in the form of a signal from the conductivity meter 272 to the microprocessor, and, in response, the microprocessor sends signals to the pumps 268, 274 and the valves 276, 278 to cause the infusate solution, the sodium chloride solution, and/or the dilution water to be introduced into the fluid line 265.

The microprocessor is also connected to the fluid detectors 269, 275. Upon detecting an absence of fluid within their respective lines, the fluid detectors 269, 275 can transmit a signal to the microprocessor, which can shut down the system or provide an indication (e.g., an audible and/or visual indication) to the user that the infusate container 228 and/or the sodium chloride container 230 are empty. In response, the user can, for example, replace or refill the infusate container 228 and/or the sodium chloride container 230.

After passing through the conductivity meter 272, the dialysate passes through a check valve 279 and into the ammonium sensor 264, which detects ammonium levels within the dialysate. If the ammonium levels within the dialysate are within an acceptable range, the dialysate is allowed to flow into the bag 238.

After filling the bag 238 to a desired level with dialysate having a desired concentration of calcium, magnesium, potassium, and sodium, a pump 280 is activated to draw the dialysate from the bag 238 into the dialysis machine 30. The dialysate is circulated through the dialysis machine 30 where it passes through a dialyzer. At the same time, a patient's blood is passed through the dialyzer. As a result, toxins, such as urea, are transferred across a permeable membrane of the dialyzer from the patient's blood to the dialysate. The spent dialysate exiting the dialyzer is then routed back to the module 220.

The spent dialysate passes through a fluid line 282 in the module 220. Depending on the desired volume of dialysate to be cycled back to the dialysis machine, some of the spent dialysate can be routed to the bag 238 by opening valve 284 and closing valve 286 as the spent dialysate is forced through the fluid line 282. As a result of the dialysis, for example, fluid from the patient may be added to the dialysate as the dialysate passes through the dialyzer of the dialysis machine 30. Thus, routing some of the spent dialysate to the bag 238 can help to ensure that a substantially constant volume of dialysate is circulated through the module 220 and the dialysis machine 30 throughout treatment. The pump 256 in the fluid line 282 forces the volume of the spent dialysate that is not routed to the bag 238 into the sorbent cartridge 24 via the base 304 of the cartridge holder 300. As the spent dialysate passes through the sorbent cartridge 24, urea is removed from the spent dialysate. Calcium, magnesium, and potassium are also stripped from the spent dialysate by the sorbent cartridge 24. The recycled dialysate or cartridge effluent, upon exiting the sorbent cartridge 24, passes through the bubble trap 264 where gases that may be produced as a result of chemical reactions within the sorbent cartridge 24 can be removed from the recycled dialysate. In the manner discussed above, after the recycled dialysate exits the sorbent cartridge 24, the infusate solution is introduced into the recycled dialysate and, based on the conductivity reading at the conductivity meter 272, sodium chloride or dilution water can be added to the recycled dialysate. In the initial stages of treatment, sodium levels in the recycled dialysate tend to be lower than desired due to the sorbent cartridge's tendency to strip sodium from fluids passing therethrough. Consequently, in the early stages of the treatment, sodium chloride will typically be injected into fluid line to increase the concentration of sodium in the recycled dialysate. In later stages of the treatment, however, the sorbent cartridge may contain high levels of sodium and thus start releasing sodium into the spent dialysate as it passes through the sorbent cartridge. This can lead to higher than desired levels of sodium in the recycled dialysate passing through the fluid line 265, resulting in an injection of dilution water into the recycled dialysate.

The recycled dialysate then passes through the check valve 279 and into the ammonium sensor 246. The ammonium sensor 246 can help to determine the state of the sorbent cartridge 24. For example, as the sorbent cartridge 24 is used, the ammonium levels in the dialysate will increase. Upon reaching a predetermined ammonium level, the treatment can be terminated. Alternatively, upon reaching the predetermined ammonium level, the sorbent cartridge 24 can be replaced with a fresh sorbent cartridge and treatment can resume.

After exiting the ammonium sensor, the recycled dialysate is routed to the bag 238 and/or the dialysis machine 30. For example, in order to ensure that an equal amount of fluid enters and exits the dialysis machine 30, a T-valve 281 can be adapted to route a portion of the dialysate to the dialysis machine 30 via fluid line 283 and to route any excess dialysate to the fresh dialysate chamber of the bag 238. If the flow rate of the dialysate at the T-valve 281 is greater than the rate at which the dialysate is being pulled into the dialysis machine 30, some of the dialysate will be routed to the bag 238. If, on the other hand, the flow rate of the dialysate at the T-valve 281 is less than the rate at which the dialysate is being pulled into the dialysis machine 30, the dialysis machine 30 will pull some of the dialysate from the bag 238. The bag 238 is formed of a flexible material and thus acts as a compliance chamber. In particular, as the dialysate is added to the bag 238, the volume of the bag 238 is allowed to increase, and, as the dialysate is removed from the bag 238, the volume of the bag 238 is allowed to decrease.

The dialysate that is delivered to the dialysis machine 30 again passes through the dialyzer where toxins are transferred from the patient's blood to the dialysate. The spent dialysate is then routed back to the module and the process is repeated until a desired amount of toxins has been removed from the patient's blood.

During treatment, an ultrafiltration process may also be performed to remove water from the patient's blood. During ultrafiltration, a pressure gradient is created across the membrane between the dialysate side and the blood side of the dialyzer. As a result, fluid is drawn across the membrane from the blood side to the dialysate side. This fluid exits the dialysis machine 30 and passes though the module 220 via a fluid line 288 and is routed to a drain bag 252. This ultrafiltration process can be continued until a desired volume of fluid has been removed from the patient.

After completing the patient's treatment, the dialysate can be removed from the bag 238. For example, the pump 256 can be activated with the valves 262, 263, 284 open and the valves 260, 286 closed. As a result, the dialysate flows from the bag 238 into the drain bag 252. Emptying the bag 238 can allow the user to more easily handle the bag 238 after treatment due to the decreased weight. In some cases, eight liters or more of dialysate is removed from the bag 238 prior to disconnecting the bag 238 from the module 220.

After draining the bag 238 to a desired level, the external components (e.g., the sorbent cartridge 24, the infusate container 228, the sodium chloride container 230, the bag 238, the dialysate bag 250, and their associated fluid lines) are disconnected from the module 220 and discarded. The manifolds 222, 232, and 230 (shown in FIGS. 5 and 7) to which the sorbent cartridge 24, the infusate container 228, the sodium chloride container 230, and the bag 238 were fluidly connected are closed so that fluid cannot flow out of the module 220 through the fluid line connection ports of the manifolds 222, 232, and 230. A bag of rinsing solution is then connected to the fluid connection port of the manifold 248 (shown in FIGS. 5 and 7) where the dialysate bag 250 was previously connected, and rinsing solution (e.g., water) is circulated through the module 220 and the dialysis machine 30 to rinse the fluid conduits within the module 220 and the dialysis machine 30. The rinsing process is carried out by drawing the rinsing solution from the rinsing solution bag into the fluid line 282 by activating the pump 256 with valves 258 and 260 open. The rinsing solution moves along the fluid line 282 to the cartridge holder 300, which is in a closed configuration (with the sorbent cartridge 24 removed) such that the fittings on the base 304 and the arm 306 of the cartridge holder are connected to the ports 318 and 320 of the bypass component 316, as shown in FIGS. 7 and 8. The various pumps and valves of the module 220 and the dialysis machine 30 are then activated in a manner to cause the rinsing solution to pass through the various fluid conduits of the module 220 and the dialysis machine 30. The rinsing solution can be collected in the drain bag 252 after passing through the various desired fluid conduits of the module 220 and the dialysis machine 30.

As an alternative to or in addition to passing the rinsing solution through the module 220 and the dialysis machine 30, a cleaning solution (e.g., bleach) can be circulated though the module 220 and the dialysis machine 30 in a similar manner to disinfect the various fluid conduits of the module and the dialysis machine.

In certain embodiments, a fluid (e.g., a rinsing solution, a cleaning solution, or dialysate left in the fluid conduits of the module 220 and the dialysis machine 30 after treatment) can be passed through the dialysis machine 30 where it is heated to a temperature of about 85 degrees Celsius. The heated fluid can be circulated through the module 220 and the dialysis machine 30 to disinfect the fluid conduits within those devices.

While the infusate container 228 has been described as being positioned upstream of the sodium chloride container 230, in some embodiments, the positions of the infusate container 228 and the sodium chloride container 230 are reversed such that the infusate container 228 is positioned downstream of the sodium chloride container 230.

In some embodiments, the bag 238 is connected to the bubble trap 264 via an additional fluid line extending from the portion of the bag 238 that contains spent dialysate to the bubble trap 264. In such embodiments, the fluid line 283 that leads to the dialysis machine 30 can extend into the portion of the bag 238 containing the fresh dialysate instead of being connected to the T-valve 281. During use, fresh dialysate is first forced into the fresh dialysate chamber of the bag 238, and then in a subsequent action the fresh dialysate is drawn from the bag 238 into the dialysis machine 230 via the fluid line 283. Because the pressure is regulated within the bag 238 as a result of the bag's connection to the bubble trap, the check valve 279 prior to the ammonium sensor 246 can be removed from the fluid loop.

While the external components (e.g., the sorbent cartridge 24, the infusate container 228, the sodium chloride container 230, the bag 238, the dialysate bag 250, the drain bag 252, the rinsing solution bag, the cleaning solution bag, and their associated fluid lines) connected to the module 220 have been described as being disposable, single use disposable components, one or more of the external components can alternatively be reusable. For example, they can be constructed to withstand disinfection techniques, such as autoclave disinfection.

While the module 220 has been described as being connected to the drain bag 252 via the manifold 248, the module can alternatively or additionally be connected directly to a drain via the manifold 248.

While the system 200 has been described as being initially primed with dialysate from the dialysate bag 250, the system can alternatively or additionally be attached to a water source and can be adapted to convert water from the water source into dialysate. In certain embodiments, for example, the dialysis machine 30 is adapted to spike the water passing therethrough with one or more concentrates to form dialysate.

In some embodiments, the module 220 alternatively or additionally includes conductivity meters positioned slightly upstream of the sodium chloride container 230 and/or slightly upstream of the infusate solution container 228. These conductivity meters can further help to ensure that desired amounts of the sodium chloride solution and/or the infusate solution is delivered to the fluid passing through the fluid line 265.

While certain methods described above include controlling the rate at which the infusate solution is introduced into the fluid line 265 based on the flow rate of the dialysate detected at the flow meter 261, other techniques are possible. In certain embodiments, for example, the weight of the infusate container 228 and the weight of the dialysate bag 238 are measured (e.g., be a weight scale), and the flow rate of the infusate is controlled based on these readings. In certain embodiments, the weight of the drain bag 252 can also be measured and accounted for when determining the appropriate flow rate of the infusate solution.

While the module 220 has been described as including pumps 268, 274 for moving the infusate solution and the sodium chloride solution from their respective containers to the fluid line 265, other techniques can alternatively or additionally be used. In certain embodiments, for example, a vacuum is used to draw the infusate solution and the sodium chloride solution from their respective containers into the fluid line 265. The flow rate of the dialysate within the fluid line 265 can, for example, create a vacuum that draws the solutions into the fluid line 265. In some embodiments, venturi tubes are provided along the fluid line 265 at the locations where the lines extending from the infusate solution container 228 and the sodium chloride solution container 230 join the fluid line 265. The venturi tubes can help to ensure that a sufficient vacuum is created to draw the solutions into the fluid line 265 from their respective containers. In embodiments, that use a vacuum to draw the solutions from their respective containers, a valve can be provided within the lines leading from the infusate solution container 228 and the sodium chloride solution container 230 to control the flow rates of the infusate solution and the sodium chloride solution into the fluid line 265. These valves can be connected to and controlled by the microprocessor in the module 220.

In addition to the components discussed above, the module 220 can further include various fluid detectors to confirm that fluid is passing through a particular fluid line or component at a desired time, flow meters to help ensure that fluid is passing through a particular fluid line or component at a desired rate, and filters to filter fluid passing through a particular fluid line or component. In certain embodiments, these additional components can be connected to the microprocessor of the module 220 such that other components, such as pumps and valves, of the module 220 can be adjusted based on the readings of these additional components.

While the systems described above use the sorbent cartridge 24 to remove toxins from the spent dialysate, other types of devices can alternatively or additionally be used to remove toxins from the spent dialysate.

While the modules described herein have been described as being coupled to the dialysis apparatus 30, other arrangements are possible. In some embodiments, for example, the module is incorporated into the dialysis apparatus. Alternatively, the module can be a stand-alone unit.

While certain devices and methods disclosed herein have been described as being used in conjunction with hemodialysis, they can be used in various other renal treatments. The principles described herein can be applicable to the particular type of hemodialysis apparatus described herein, and to a variety of other dialysis apparatus having similar functions.

EXAMPLES

The following data was collected based on use of a dialysis system of the type shown in FIG. 1 above.

For the initial setup, fluid was recirculated from the spent reservoir via the recirculation pump, into the bottom of the sorbent cartridge. The effluent from the cartridge was then directed into the fresh reservoir. Fluid from the fresh reservoir was pumped to the dialysis machine via the pressure pump where it was processed in the normal manner for the dialysis machine. The flow rate for the dialysis machine was set to 200 cc/min and the sorbent cartridge recirculation was at 225 cc/min.

The simulated patient contained 42 liters of deionized water with 244 g of NaCl, 135.5 g of NaHCO3, 30 g Urea, 15 g KCl, 27.26 g of Sorb Concentrate containing Calcium Acetate and Magnesium Acetate. The initial chemistry values for the simulated patient were: Na 132.7 mg/dL, Cl 100.9 mg/dL, K 4.53 mg/dL, Ca 5.88 mg/dL, Mg 2.0 mg/dL, Urea Nitrogen 33.3 mg/dL (note that a typical pre-blood urea nitrogen value is approximately 60 mg/dL, i.e., twice this amount).

To attain a base sodium in the reservoirs, the spent reservoir was spiked with 68.25 g NaCl. The system was allowed to stabilize and ran for 4 hours. Samples were taken directly out of the sorbent cartridge prior to entering the fresh reservoir (Na Fm Sorb), at the inlet dialysate connector (Na to Pt) and from the Arterial Line Pre-Pump (Na Pt)

Figure 10:
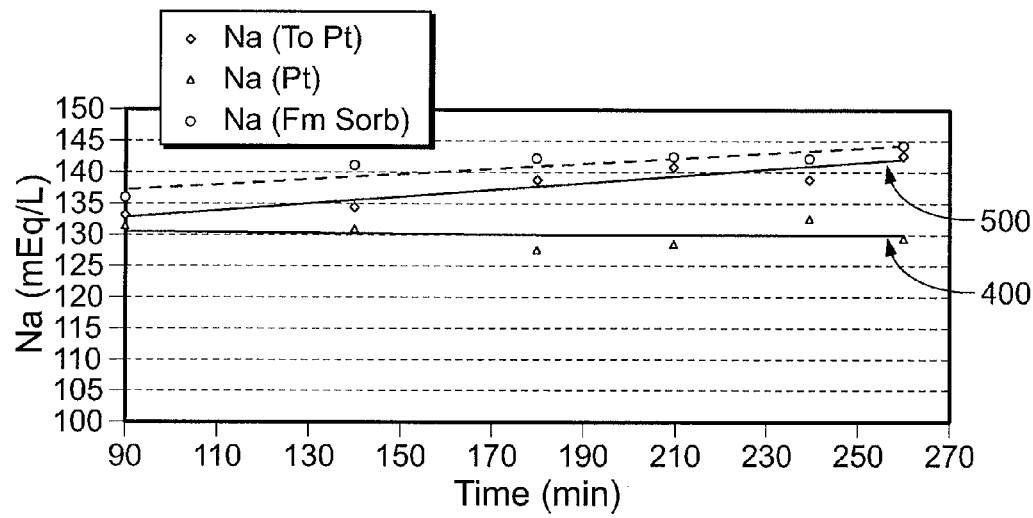
FIG. 10 is a graph illustrating sodium changes during a four hour simulated patient run.

As can be seen in the graph in FIG. 10, the sodium levels of the patient (line 400) initially dipped then came back up and remained relatively stable. The sodium in the "to patient" line (line 500) increased from a 133.8 mEq/L at 90 minutes to 138.8 mEq/L at 240 minutes, for an increase of 5 mEq/L. In the "Sorbent Dialysis Primer" (Cobe Renal Care, Inc.; Ed. 4; 1993), graph 2.1 illustrated that for the average adult renal patient with a normal or near normal pre-dialysis sodium, the dialysate would increase from 139 mEq/L at 90 minutes to 160 mEq/L at 240 minutes, an increase of 21 mEq/L.

Figure 11:
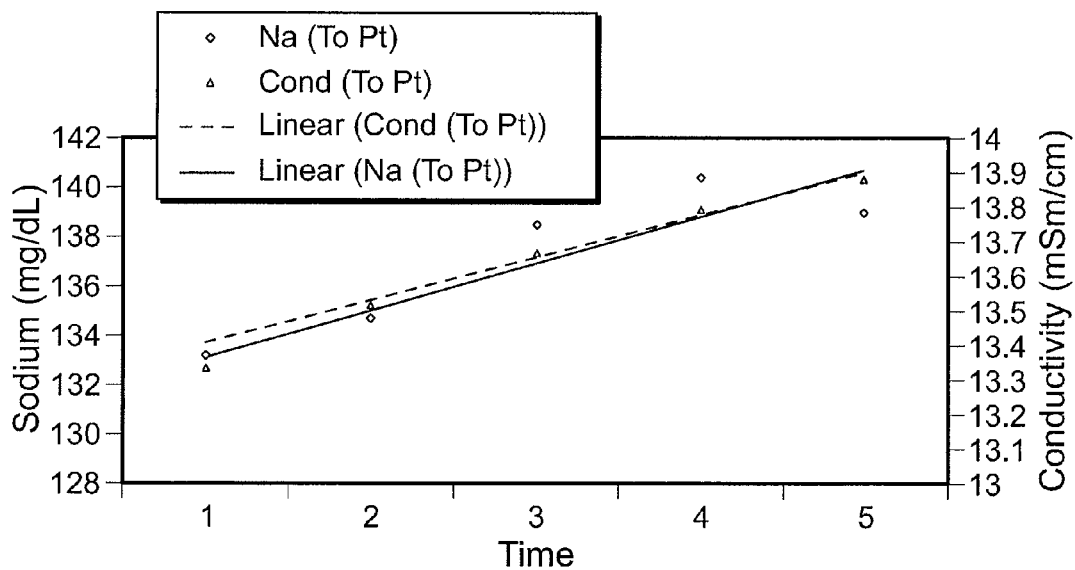
FIG. 11 is a graph illustrating conductivity versus sodium levels during a four hour simulated patient run.

Since calcium, magnesium and potassium are removed by the sorbent cartridge, the changes to conductivity going to the patient should be directly proportional to the sodium change resulting from the sorbent cartridge. This is illustrated in the data collected and shown in the graph of FIG. 11.

To further test the dilution method to show that it can work, a sorbent cartridge was setup as described in the initial setup (FIG. 1) above. The system was allowed to stabilize for approximately one hour. Upon stabilization, 60 cc of deionized water was injected into the fresh reservoir and the conductivity was observed coming from the sorbent cartridge and at the Dialysate Inlet Port of the dialyzer connected to the simulated patient.

Figure 12:
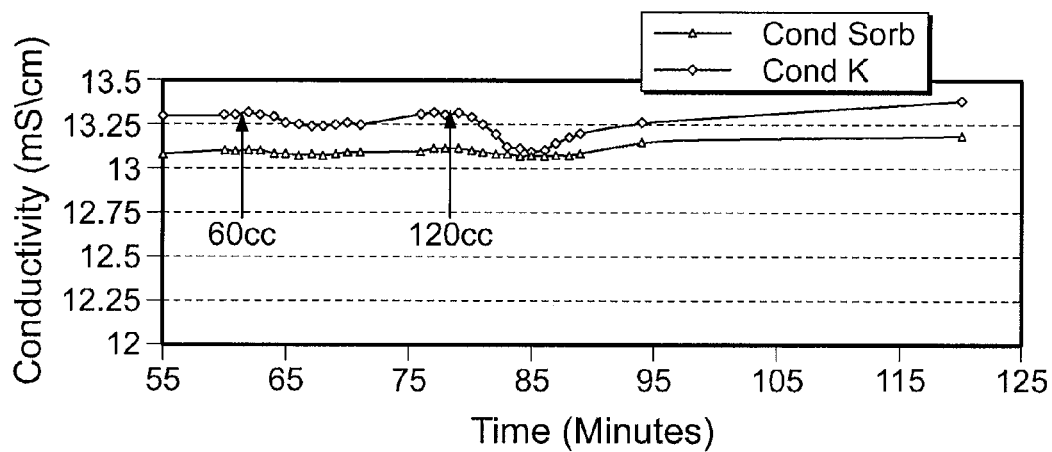
FIG. 12 is a graph illustrating conductivity response to deionized bolus injections during a four hour simulated patient run.

As can be seen in the graph of FIG. 12, the conductivity (hence the sodium) decreased from 13.3 mS/cm to 13.25 mS/Cm and recovered after approximately 15 minutes. A 120 cc bolus of DI water caused the conductivity going to the patient to decrease from 13.3 mS/cm to 13.12 mS/cm and took approximately 30 minutes to recover.

Figure 13:
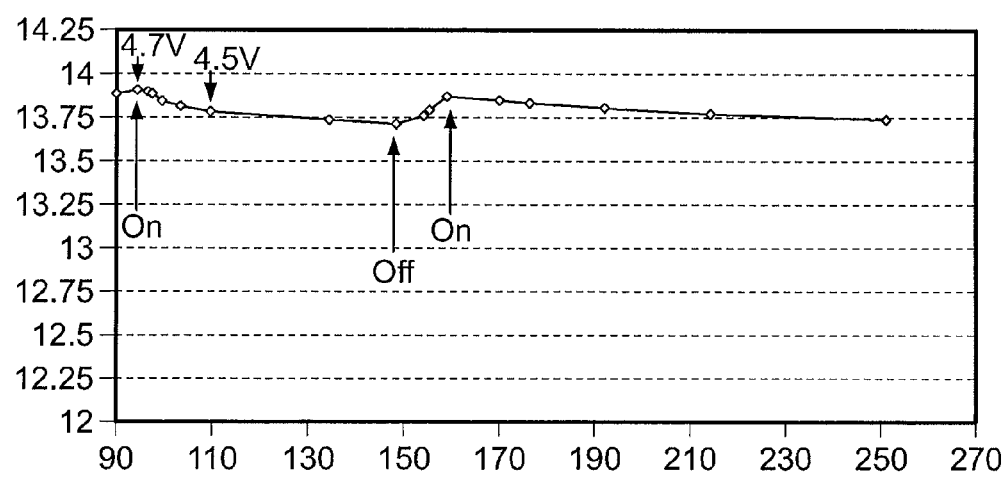
FIG. 13 is a graph illustrating conductivity response to continuous dilution during a four hour simulated patient run.

The graph in FIG. 13 shows conductivity control using a metering pump attached to a peritoneal dialysis bag. The bag was first filled using a three way valve and diverting the output of the sorbent cartridge to the bag prior to adding the base sodium chloride to the bath. Conductivity (i.e. the sodium) could be varied throughout the four hour run. Initially the metering pump was set too high, and the conductivity was dropping. After adjustment of the voltage to the metering pump from 4.7 V to 4.5V, the conductivity stabilized. To demonstrate that the sodium would have been rising in the absence of the dilution, the metering pump was turned off approximately 150 min into the run.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

Other embodiments are within the scope of the following claims.

What is claimed is:

1. A dialysis system, comprising:
a dialysis machine; and
a module that is directly, fluidly coupled to the dialysis machine via a fluid inlet line and a fluid outlet line such that dialysis solution flows directly from the module to the dialysis machine, through the dialysis machine, and directly from the dialysis machine back to the module, the module being electrically coupled to the dialysis machine and fluidly coupled to a dialysis solution reservoir, the module retaining a device in a manner such that dialysis solution can pass through the device, the device being adapted to remove one or more substances from the dialysis solution as the dialysis solution passes through the device, the module comprising
a fluid line connected to the device, the fluid line being arranged so that dialysis solution exiting the device passes through the fluid line, and
a sodium control system in fluid communication with the fluid line, the sodium control system being adapted to alter a sodium concentration of dialysis solution passing through the fluid line,
wherein the dialysis system controls a flow rate of dialysis solution from the module to the dialysis machine in a manner such that dialysis solution is diverted to the dialysis solution reservoir if an actual flow rate of dialysis solution from the module to the dialysis machine is greater than a desired flow rate and dialysis solution is drawn from the dialysis solution reservoir if the actual flow rate of dialysis solution from the module to the dialysis machine is less than the desired flow rate.

2. The dialysis system of claim 1, wherein the sodium control system is adapted to introduce a diluent into the fluid line.

3. The dialysis system of claim 2, wherein the diluent comprises water.

4. The dialysis system of claim 2, wherein the sodium control system comprises a container that contains the diluent, and the sodium control system further comprises a pump arranged to move the diluent from the container to the fluid line.

5. The dialysis system of claim 1, wherein the sodium control system is adapted to introduce sodium into the fluid line.

6. The dialysis system of claim 5, wherein the sodium is in the form of a sodium chloride solution.

7. The dialysis system of claim 5, wherein the sodium control system comprises a container that contains a sodium solution, and the sodium control system is adapted to draw the sodium solution from the container to the fluid line using vacuum.

8. The dialysis system of claim 5, wherein the sodium control system comprises a container that contains a sodium solution, and the sodium control system further comprises a pump arranged to move the sodium solution from the container to the fluid line.

9. The dialysis system of claim 8, wherein the sodium control system further comprises a diluent source, and the pump is arranged to move diluent from the diluent source to the fluid line.

10. The dialysis system of claim 9, wherein the diluent source is a fluid line that contains pressurized diluent.

11. The dialysis system of claim 9, wherein the sodium control system further comprises one or more valves that can be actuated to control movement of the sodium solution and the diluent to the fluid line.

12. The dialysis system of claim 1, further comprising a conductivity meter that is adapted to measure conductivity of the solution passing through the fluid line, the conductivity meter being in communication with the sodium control system.

13. The dialysis system of claim 12, wherein the sodium control system is adapted to alter the sodium concentration of the solution passing through the fluid line based on an output signal of the conductivity meter.

14. The dialysis system of claim 1, wherein the device is a sorbent cartridge.

15. The dialysis system of claim 14, wherein the sorbent cartridge comprises at least one layer of material capable of regenerating spent dialysis solution.

16. The dialysis system of claim 15, wherein a layer of the sorbent cartridge comprises sodium zirconium carbonate.

17. The dialysis system of claim 1, wherein the dialysis solution reservoir is a dual compartment reservoir.

18. The dialysis system of claim 17, wherein the dual compartment reservoir comprises a first reservoir for spent dialysis solution and a second reservoir for fresh dialysis solution.

19. The dialysis system of claim 18, further comprising an input line and an output line, the input and output lines being in fluid communication with the second reservoir, the input line being arranged to deliver fresh dialysis solution into the second reservoir and the output line being arranged to remove fresh dialysis solution from the second reservoir.

20. The dialysis system of claim 18, further comprising an input/output line, the input/output line being in fluid communication with the second reservoir, the input/output line being arranged to deliver fresh dialysis solution into the second reservoir and to remove fresh dialysis solution from the second reservoir.

21. The dialysis system of claim 1, further comprising an infusate system in fluid communication with the fluid line, the infusate system being adapted to introduce an infusate solution into the fluid line.

22. The dialysis system of claim 21, wherein the infusate solution comprises magnesium, calcium, and potassium.

23. The dialysis system of claim 21, further comprising a flow meter arranged to detect a flow rate of the dialysis solution, the infusate system being adapted to introduce the infusate solution into the fluid line based on the flow rate of the dialysis solution.

24. The dialysis system of claim 1, wherein the device is fluidly coupled to the module.

25. The dialysis system of claim 24, wherein the module comprises a device holder that can be arranged in a first configuration to allow fluid to pass through the device or in a second configuration to allow fluid to pass from a first portion of the device holder to a second portion of the device holder without passing through the device.

26. A dialysis apparatus, comprising:
a module that is releasably, directly, fluidly coupled to a dialysis machine via a fluid inlet line and a fluid outlet line such that dialysis solution flows directly from the module to the dialysis machine, through the dialysis machine, and directly from the dialysis machine back to the module, the module being electrically coupled to the dialysis machine and fluidly coupled to a dialysis solution reservoir, the module retaining a device adapted to remove one or more substances from a dialysis solution as the dialysis solution passes through the device after exiting the dialysis machine,
wherein the dialysis apparatus controls a flow rate of dialysis solution from the module to the dialysis machine in a manner such that dialysis solution is diverted to the dialysis solution reservoir if an actual flow rate of dialysis solution from the module to the dialysis machine is greater than a desired flow rate and dialysis solution is drawn from the dialysis solution reservoir if the actual flow rate of dialysis solution from the module to the dialysis machine is less than the desired flow rate.

27. The dialysis apparatus of claim 26, wherein the dialysis machine is a hemodialysis machine.

28. The dialysis apparatus of claim 26, wherein the device is a sorbent cartridge.

29. The dialysis apparatus of claim 26, wherein the module further comprises a sodium control system that is adapted to alter a sodium concentration of the dialysis solution.

30. The dialysis apparatus of claim 29, wherein the sodium control system is arranged to alter the sodium concentration of the dialysis solution after the dialysis solution passes through the device.

31. The dialysis apparatus of claim 26, wherein the module further comprises an infusate system that is adapted to introduce an infusate solution into the dialysis solution.

32. The dialysis apparatus of claim 31, wherein the infusate solution comprises magnesium, calcium, and potassium.

33. The dialysis apparatus of claim 31, wherein the infusate system is arranged to introduce the infusate solution into the dialysis solution after the dialysis solution passes through the device.

34. The dialysis apparatus of claim 26, wherein the module comprises a pump adapted to move the dialysis solution from the module to the dialysis machine when the module is fluidly coupled to the dialysis machine.

35. The dialysis apparatus of claim 26, wherein the module is releasably, directly, fluidly and electrically coupled to any of a plurality of different dialysis machines.

36. The dialysis system of claim 1, wherein the module is releasably, directly, fluidly and electrically coupled to the dialysis machine.

37. The dialysis system of claim 18, wherein the first and second reservoirs are configured so that fresh dialysis solution overflows from the second reservoir into the first reservoir when the second reservoir is filled beyond its capacity with the fresh dialysis solution.

38. The dialysis apparatus of claim 26, wherein the dialysis solution reservoir is a dual compartment reservoir.

39. The dialysis apparatus of claim 38, wherein the dual compartment reservoir comprises a first reservoir for spent dialysis solution and a second reservoir for fresh dialysis solution.

40. The dialysis apparatus of claim 39, further comprising an input line and an output line, the input and output lines being in fluid communication with the second reservoir, the input line being arranged to deliver fresh dialysis solution into the second reservoir and the output line being arranged to remove fresh dialysis solution from the second reservoir.

41. The dialysis apparatus of claim 39, further comprising an input/output line, the input/output line being in fluid communication with the second reservoir, the input/output line being arranged to deliver fresh dialysis solution into the second reservoir and to remove fresh dialysis solution from the second reservoir.

42. The dialysis apparatus of claim 39, wherein the first and second reservoirs are configured so that fresh dialysis solution overflows from the second reservoir into the first reservoir when the second reservoir is filled beyond its capacity with the fresh dialysis solution.

43. The dialysis system of claim 1, wherein the dialysis system further comprises a T-valve that is fluidly coupled to the fluid line and is arranged so that dialysis solution is diverted from the fluid line to the dialysis solution reservoir if the actual flow rate of the dialysis solution from the module to the dialysis machine is greater than the desired flow rate and so that dialysis solution is drawn from the dialysis solution reservoir if the actual flow rate of the dialysis solution from the module to the dialysis machine is less than the desired flow rate.

44. The dialysis apparatus of claim 26, wherein the dialysis apparatus further comprises a T-valve that is fluidly coupled to the fluid line and is arranged so that dialysis solution is diverted from the fluid line to the dialysis solution reservoir if the actual flow rate of the dialysis solution from the module to the dialysis machine is greater than the desired flow rate and so that dialysis solution is drawn from the dialysis solution reservoir if the actual flow rate of the dialysis solution from the module to the dialysis machine is less than the desired flow rate.

45. The dialysis system of claim 1, wherein the sodium control system is spaced apart from the dialysis solution reservoir and from the device.

46. The dialysis apparatus of claim 29, wherein the sodium control system is spaced apart from the dialysis solution reservoir and from the device.

* * * * *